United States Patent
Van Oudenallen et al.

(10) Patent No.: US 9,320,642 B1
(45) Date of Patent: Apr. 26, 2016

(54) METHOD OF AND SYSTEM FOR SELECTING PATIENT TEMPERATURE REGULATION TOOLS

(75) Inventors: Robertus Gerardus Van Oudenallen, Vleuten (NL); Berend Jan Teunissen, Haaksbergen (NL)

(73) Assignee: THE SURGICAL COMPANY INTERNATIONAL B.V., Amersfoort (NL)

( * ) Notice: Subject to any disclaimer, the term of this patent is extended or adjusted under 35 U.S.C. 154(b) by 237 days.

(21) Appl. No.: 13/487,825

(22) Filed: Jun. 4, 2012

(51) Int. Cl.
*A61F 7/00* (2006.01)
*G06F 19/00* (2011.01)

(52) U.S. Cl.
CPC .............. *A61F 7/00* (2013.01); *G06F 19/3406* (2013.01); *G06F 19/3418* (2013.01)

(58) Field of Classification Search
CPC ...... A61B 5/0002; A61B 5/0205; A61B 5/01; A61B 5/14532; A61B 5/14865; A61B 5/1495; A61B 5/0008; A61B 5/015; A61B 5/6804; A61B 5/103; A61B 5/107; A61B 19/56; A61B 2010/0019; A61B 2576/00; G06F 19/3418; G06F 19/3406; G06Q 50/24; A61F 7/00; A61F 7/0097; A61F 7/08; A61F 7/12; A61F 2007/0093; A61F 2007/0095; G01K 1/02; G01K 1/024; G01K 13/002; G01N 25/18; G01N 33/36; G01N 33/367; H05B 3/342; H05B 2203/036; G05D 23/1931
USPC ................. 600/301, 315, 347, 549, 306, 474; 701/36; 705/3; 700/299, 130, 300; 374/29, 30, 4, 44, 100, 132–135, 137, 374/138; 219/200, 201, 211, 212, 520, 219/527–529; 702/127, 130–132, 136; 165/11.1, 11.2, 200, 201, 253, 279
See application file for complete search history.

(56) References Cited

U.S. PATENT DOCUMENTS

| | | | | |
|---|---|---|---|---|
| 5,046,505 | A * | 9/1991 | Sekii et al. | 600/326 |
| 5,241,965 | A * | 9/1993 | Mick | 600/526 |
| 6,048,304 | A * | 4/2000 | Koch | 600/22 |
| 6,409,653 | B1 * | 6/2002 | Koch et al. | 600/22 |
| 6,581,677 | B2 * | 6/2003 | Dukes-Dobos et al. | 165/11.1 |
| 7,211,105 | B2 * | 5/2007 | Magers et | 607/105 |
| 7,216,068 | B2 * | 5/2007 | Li et al. | 703/6 |
| 7,226,426 | B2 * | 6/2007 | Thomson | 600/595 |
| 7,313,447 | B2 * | 12/2007 | Hsiung | G05B 15/02 700/17 |
| 7,340,293 | B2 * | 3/2008 | McQuilkin | 600/474 |
| 7,404,140 | B2 * | 7/2008 | O'Rourke | 715/222 |
| 7,785,266 | B2 * | 8/2010 | Fraden | 600/549 |
| 7,787,938 | B2 * | 8/2010 | Pompei | 600/474 |
| 7,816,628 | B2 * | 10/2010 | Fernandez et al. | 219/211 |

(Continued)

*Primary Examiner* — Crystal J Barnes-Bullock
(74) *Attorney, Agent, or Firm* — Nixon & Vanderhye P.C.

(57) ABSTRACT

The invention provides a method of selecting one or more patient temperature regulation tools is provided. The method comprises: providing a database storing one or more properties of each of a plurality of temperature regulation tools; selecting one or more patient temperature regulation tools from the database; calculating an estimated patient heat balance taking into account one or more of the one or more properties of the selected patient temperature regulation tool (s); providing an indication of the estimated patient heat balance; and providing a visual aid illustrating the one or more selected patient temperature regulation tools regulating the temperature of a patient. The method may be used for selecting one or more patient temperature tools for a patient who is to undergo a medical procedure. Additionally or alternatively, the method may be use as an e-learning tool.

43 Claims, 9 Drawing Sheets

(56) References Cited

U.S. PATENT DOCUMENTS

| | | | |
|---|---|---|---|
| 7,942,825 B2* | 5/2011 | Ranganathan et al. | 600/549 |
| 7,997,793 B2* | 8/2011 | Stone et al. | 374/164 |
| 8,073,535 B2* | 12/2011 | Jung et al. | 600/547 |
| 8,577,642 B2* | 11/2013 | Pompei et al. | 702/131 |
| 8,606,344 B2* | 12/2013 | DiMaio et al. | 600/407 |
| 8,663,106 B2* | 3/2014 | Stivoric et al. | 600/301 |
| 8,706,207 B2* | 4/2014 | Flint | 600/546 |
| 9,015,001 B2* | 4/2015 | Shimizu | G01K 1/165 702/131 |
| 2004/0242976 A1* | 12/2004 | Abreu | 600/315 |
| 2009/0099629 A1* | 4/2009 | Carson et al. | 607/96 |
| 2009/0105605 A1* | 4/2009 | Abreu | 600/549 |
| 2009/0275808 A1* | 11/2009 | DiMaio et al. | 600/301 |
| 2009/0306748 A1* | 12/2009 | Mollendorf | A61F 7/00 607/104 |
| 2010/0087900 A1* | 4/2010 | Flint | 607/104 |
| 2013/0030411 A1* | 1/2013 | Kreck | A61F 7/12 604/514 |
| 2015/0217079 A1* | 8/2015 | Mcauley | A61M 16/109 128/203.14 |

* cited by examiner

METHOD OF AND SYSTEM FOR SELECTING PATIENT TEMPERATURE REGULATION TOOLS

FIELD OF THE INVENTION

The invention relates to a method of and system for selecting patient temperature regulation tools. The invention also relates to a computer readable medium storing a computer program product, and an e-learning application, for performing said method.

BACKGROUND TO THE INVENTION

Modern medicine recognises the importance of managing the temperature of patients before, during and after surgical and other medical procedures. Successful patient temperature management can improve patient outcome and reduce patient recovery time.

Patient temperature management can be modelled by considering the heat balance of a patient, that is to say, the rate of gain or loss of heat by the patient. A patient's heat balance may be affected by for example anaesthesia, patient parameters (such as age and gender), environmental conditions (such as ambient temperature and pressure), the proportion of a patient's body which is uncovered, the temperature of fluids introduced into the body and so forth.

A wide range of patient temperature regulation tools are known which can be used to regulate the heat balance of patients undergoing medical/surgical procedures. These include passive insulating tools (e.g. blankets and garments such as gowns, socks or caps) and active warming tools (e.g. forced air warming blankets).

In order to select appropriate tools for regulating the heat balance of patients undergoing a particular medical procedure, the thermal properties of the patient temperature regulation tools may be matched with metrics calculated from anaesthetic parameters, patient parameters and/or specified environmental conditions. However, this may result in the selection of a plurality of tools which are incompatible with each other, or of one or more tools which are incompatible with the particular patient and/or with the particular medical/surgical procedure a patient is to undergo.

Furthermore it is typically necessary to train relevant medical personnel to make them aware of what tools are available, the relevant thermal properties of those tools and how those tools may be used to regulate the heat balance of a patient. However, a wide range of products is available, and new products are regularly developed. It can therefore be difficult for personnel to develop an understanding of the effect of the various patient warming tools which are available and their inter-relationship.

Accordingly, the invention seeks to provide an improved method of and system for selecting appropriate patient temperature regulation tools. Some embodiments of the invention are also useful as training tools which may be used for the training of medical personnel with respect to new and existing patient temperature regulation tools.

SUMMARY OF THE INVENTION

A first aspect of the invention provides a method of selecting one or more patient temperature regulation tools, the method comprising: providing a database storing one or more properties of each of a plurality of temperature regulation tools; selecting one or more patient temperature regulation tools from the database; calculating an estimated patient heat balance taking into account one or more of the one or more properties of the selected patient temperature regulation tool(s); providing an indication of the estimated patient heat balance; and providing a visual aid illustrating the one or more selected patient temperature regulation tools regulating the temperature of a patient.

By providing both an indication of the estimated patient heat balance and a visual aid illustrating the one or more selected patient temperature regulation tools regulating the patient's temperature, it can be readily determined whether or not the selected patient temperature regulation tools is/are suitable for use on a particular patient and/or in a particular medical procedure.

In some circumstances, the one or more selected patient temperature regulation tools will have thermal properties suitable for sufficiently regulating the temperature of a patient. However, one or more of the selected patient temperature regulation tools may be unsuitable for use with a particular patient and/or a particular medical procedure. For example, the tool may comprise a pair of heated leggings, which may be unsuitable for use on a patient undergoing knee surgery.

Additionally or alternatively, a plurality of selected patient temperature regulation tools may be unsuitable for use together. The visual aid provides further information, beyond the thermal properties of the selected patient temperature regulation tool(s), which allows a more thorough (but rapid) analysis to be undertaken by a user as to whether the selected tool(s) are suitable for a particular patient and/or medical procedure and/or whether a plurality of selected patient temperature regulation tools are compatible with each other.

The one or more properties of the one or more patient temperature regulation tools typically comprise one or more thermal properties of the patient temperature regulation tools.

Patient temperature regulation tools may be active or passive tools which are provided externally with reference to the patient's body. Active patient temperature regulation tools may comprise an active element (such as a heating element) which acts as a heat source providing heat energy to a patient, or which acts as an active heat sink which takes heat away from the patient. For example active patient regulation tools may comprise forced air warming tools (which may comprise an active heating element which heats the air) which regulate a patient's temperature by projecting heated air against the patient. Passive temperature regulation tools may comprise insulators which retain heat produced internally by the patient's body in the vicinity of the body. For example, passive heat tools may comprise blankets and garments such as gowns, socks, insulating leggings or caps.

Additionally or alternatively patient regulation tools may comprise fluid warming tools for regulating the temperature of in vitro fluids. For example, fluid warming tools may comprise blood warming tools which regulate the temperature of blood before it is injected into the patient.

Preferably, the visual aid comprises a visual representation of a patient and a visual representation of the one or more selected patient temperature regulation tools regulating the patient's temperature.

A visual representation of the patient together with a visual representation of the tool(s) in the act of regulating the patient's temperature provides an informative, understandable visual aid which allows a rapid analysis to be performed as to whether the selected tool(s) are suitable for a particular patient and/or medical procedure.

Preferably, one or more of the one or more properties of the each of said plurality of patient temperature regulation tools are presented on a visual display prior to the step of selecting one or more patient temperature regulation tools from the database.

Displaying one or more properties of each of the patient temperature regulation tools within the database prior to the step of selecting one or more patient temperature regulation tools allows patient temperature regulation tools to be selected whose displayed properties are theoretically suitable for a particular patient and/or in a particular medical procedure.

Typically, the one or more properties of the patient temperature regulation tools displayed on the visual display comprise a shape of each patient temperature regulation tool, an orientation of a patient when the patient temperature regulation tool is in use and/or one or more thermal properties of the patient temperature regulation tool.

Typically the visual display is an electronic display, such as an LCD, LED or CRT monitor, tablet computer screen, smartphone screen or any other suitable display.

Preferably, the one or more displayed properties of the each of said plurality of patient temperature regulation tools and the visual aid are displayed on a common graphical user interface.

By displaying both the displayed properties of the patient temperature regulation tools which may be selected from the database and the visual aid on a common graphical user interface, the method according to the first aspect of the invention can be performed in an intuitive user-friendly manner. This is because inputs (i.e. selecting one or more patient temperature regulation tools) and outputs (visual aid) are provided on the same interface. Preferably, the displayed properties of one or more of the patient temperature regulation tools and the visual aid are displayed simultaneously.

Preferably, one or more properties of the one or more selected patient temperature regulation tools are displayed on the common graphical user interface together (e.g. simultaneously) with the visual aid as a reminder to the user of which tools were selected.

The indication of the estimated patient heat balance may be, for example, an audio indication, but preferably the indication of the estimated patient heat balance is a visual indication.

The visual indication of the estimated patient heat balance may be any suitable visual indication such as an alphanumerical display, a slide bar having a sliding indicator or a colour coded chart. A visual indication is readily understandable, and can be quickly analysed to determine whether suitable patient temperature regulation tools have been selected.

Preferably, the visual indication of the estimated patient heat balance is displayed on the common graphical user interface simultaneously with the visual aid.

By providing the visual indication of the estimated patient heat balance on the graphical user interface together with the visual aid, it can rapidly be determined whether the present selection of patient temperature regulation tools is suitable for a particular patient and/or a particular medical procedure.

Preferably, the method further comprises selecting a plurality of patient temperature regulation tools from the database; calculating an estimated net patient heat balance taking into account one or more of the one or more properties of the plurality of selected patient temperature regulation tools; and providing a visual aid illustrating the plurality of selected patient temperature regulation tools together regulating the patient's temperature.

A plurality of patient temperature regulation tools may be used in combination to regulate the temperature of a patient undergoing a medical procedure. Accordingly, it is beneficial to calculate the estimated patient heat balance taking into account the properties of a plurality of patient temperature regulation tools, and to provide a visual aid illustrating the plurality of selected patient temperature regulation tools together regulating the patient's temperature. This helps to determine whether the selected patient temperature regulation tools are compatible or incompatible with each other and/or with a particular patient and/or medical procedure.

In some embodiments, the visual aid illustrates an interaction between the plurality of selected patient temperature regulation tools.

Preferably, the visual aid comprises a visual representation of the patient and a visual representation of the plurality of selected patient temperature regulation tools together in the act of regulating the patient's temperature.

As above, a visual representation of the patient together with a visual representation of the tools in the act of regulating the patient's temperature provides an informative, understandable visual aid which allows a rapid analysis to be performed as to whether the selected tools are suitable for a particular patient and/or medical procedure.

Preferably, the method further comprises: inputting (e.g. through a user interface) one or more patient parameters; and calculating the estimated patient heat balance taking into account the inputted patient parameters.

By inputting one or more patient parameters, the calculation of the estimated patient heat balance can be customised to a particular patient. This helps to provide a more accurate calculation, which allows a more accurate indication to be provided of whether the selected tools are suitable for regulating the temperature of a particular patient.

Typically the one or more patient parameters comprise one or more patient parameters selected from the group of patient parameters consisting of: patient gender, patient mass, patient height and patient age.

Preferably, the method further comprises: inputting one or more environmental conditions relating to the environment in which the medical procedure will take place; and calculating the estimated patient heat balance taking into account the inputted environmental conditions.

By inputting one or more environmental conditions, the calculation of the estimated patient heat balance can be customised to particular environmental conditions. This helps to calculate a more accurate estimate of the patient heat balance, which allows a more accurate indication to be provided of whether the selected tools are suitable for regulating the temperature of a patient in a particular environment.

Typically the inputted environmental conditions comprise one or more environmental conditions selected from the group of environmental conditions consisting of: ambient temperature, relative humidity, ambient pressure or velocity of down flow of air within the environment where the medical procedure will take place.

Preferably, the method further comprises inputting one or more variables selected from the group of variables consisting of: a type of anaesthetics; an orientation of the patient; flow rate and temperature of applied IV-fluids; and/or parameters of a surgical wound, and calculating the estimated patient heat balance taking into account one or more of said inputted variable(s).

Again, by taking into account one or more of these variables, the calculation of the estimated patient heat balance can be customised in accordance with the inputted variables. This helps to calculate a more accurate estimate of the patient heat balance, which allows a more accurate indication to be provided of whether the selected tools are suitable for regulating the temperature of a patient under particular circumstances.

Preferably, the method further comprises inputting a type of medical procedure (e.g. through a user interface).

By inputting a type of medical procedure, one or more of the patient temperature regulation tools provided in the database may be excluded from (or recommended for) selection because they are incompatible (or compatible) with a particular type of medical procedure.

Additionally or alternatively, the type of medical procedure may determine additional information concerning, for example: an expected exposed surface area of (e.g. the body of) a patient during the medical procedure; surface area of (e.g. the body of) a patient expected to contact a mattress during the medical procedure; and/or expected heat loss from a patient during the medical procedure, on account of for example exposed patient organs and/or an anticipated surgical wound. In this case, the calculation of the estimated heat balance of the patient may take into account this additional information.

In one embodiment, the method further comprises providing a warning indication if one or more of the selected one or more patient temperature regulation tools are incompatible with the inputted type of medical procedure.

When incompatible patient temperature regulation tools are not excluded from selection, the warning indication provides an alert that one or more of the selected one or more patient temperature regulation tools are incompatible with the inputted type of medical procedure. Preferably, the warning indication indicates which of the selected tools is/are incompatible with the inputted type of procedure. The warning indication may also alert a user if a plurality of patient temperature regulation tools are selected which are incompatible with each other.

Optionally, the method further comprises: providing a recommendation of one or more patient temperature regulation tools which are compatible with the inputted type of medical procedure; and selecting one or more recommended patient temperature regulation tools.

Thus, in addition, or as an alternative, to providing a warning indication that one or more of the selected one or more patient temperature regulation tools are incompatible with the inputted type of medical procedure, a proactive recommendation of patient temperature regulation tools may be provided. Optionally, this may, but does not necessarily, involve excluding incompatible tools from selection.

Preferably, the method further comprises newly selecting one or more previously unselected patient temperature regulation tools and/or deselecting one or more previously selected patient temperature regulation tools in response to the indication of the estimated patient heat balance and/or visual aid; and calculating a new estimated patient heat balance taking into account the properties of the newly selected patient temperature regulation tools.

Typically, an updated visual aid may also be provided in response to the new selection/deselection of tools, the updated visual aid illustrating the one or more newly selected patient temperature regulation tools regulating the temperature of a patient but not the deselected patient temperature regulation tools.

In this case, the selection of patient temperature regulation tools from the database can be changed if for example the previous selection was unsuitable, and the indication of estimated patient heat balance and/or visual aid is updated accordingly. This allows experimentation between different combinations of patient temperature regulation tools in order to obtain a suitable selection of patient temperature regulation tools.

By previously selected tools, we mean those tools which were selected to calculate the heat balance that was last calculated, and by previously unselected tools we mean those tools which were not selected to calculate the heat balance that was last calculated.

Typically the estimated heat balance is calculated by calculating the sum of a plurality of discrete heat flows.

In this case, the plurality of discrete heat flows each typically represent one or more of the following: metabolic heat flow of a patient; heat flow of exposed body parts; heat flow of passive insulated body parts; heat flow of body parts actively warmed by one or more active patient temperature regulation tools; heat flow of supplied intravenous fluids; or heat flow of a surgical wound.

The method may further comprise updating the database with one or more properties of additional patient temperature regulation tools.

It will be understood that the patient is typically human, but the method may alternatively be applied to animals.

Typically, the method according to the first aspect of the invention is a computer implemented method. The method may be implemented on a plurality of computers. For example, an application may be executed on a server, with a graphical user interface being provided at a client computer in data communication with the server. Selection of one or more patient temperature regulation tools may be performed at the client computer, while the database may be stored, and the calculation of estimated patient heat balance may be performed, either at the server or at the client computer.

A second aspect of the invention provides a computer readable medium storing a computer program product for performing the method according to the first aspect of the invention.

A third aspect of the invention provides an e-learning application for performing the method according to the first aspect of the invention.

A fourth aspect of the invention provides a computer system implementing an application for selecting one or more patient temperature regulation tools, the application comprising: a database storing one or more properties of each of a plurality of patient temperature regulation tools stored in a database; an input module operable to receive a selection of one or more patient temperature regulation tools from the plurality of patient temperature regulation tools stored in the database; a calculation module operable to calculate an estimated patient heat balance taking into account one or more properties of the one or more selected patient temperature regulation tools; an indication module operable to provide an indication of the estimated patient heat balance; and a visual aid module operable to provide a visual aid illustrating the one or more selected patient temperature regulation tools regulating the temperature of a patient.

Preferably, the application further comprises a database display module operable to provide a visual indication of each of the plurality of temperature regulation tools stored in the database.

In this case, the database display module and visual aid module are preferably operable to display the visual indication and visual aid to a common graphical user interface.

Preferably, the indication module is operable to provide a visual indication of the estimated patient heat balance.

Even more preferably, the indication module is operable to display the visual indication of the estimated patient heat balance on the common graphical user interface simultaneously with the visual aid.

Preferably, the input module is operable to receive an input of one or more patient parameters and wherein the calculation module is operable to calculate the estimated patient heat balance taking into account any patient parameters input to the application.

Typically, the one or more patient parameters are selected from the group of patient parameters consisting of: patient gender, patient mass, patient height and patient age.

Preferably, the input module is operable to receive an input identifying one or more environmental conditions relating to an environment in which a patient will undergo a medical procedure, wherein the calculation module is operable to calculate the estimated patient heat balance taking into account one or more of said inputted environmental conditions.

Typically, the inputted environmental conditions comprise one or more environmental conditions selected from the group of environmental conditions consisting of: temperature, relative humidity, ambient pressure or velocity of down flow of air in the environment in which the medical procedure will take place.

The input module may further be operable to receive an input identifying one or more variables selected from the group of variables consisting of: a type of anaesthetics; an orientation of the patient; flow rate and temperature of applied IV-fluids; or parameters of a surgical wound, and calculating the estimated patient heat balance taking into account one or more of said inputted variable(s).

Preferably the input module is operable to receive an input identifying a type of medical procedure.

The application may further comprise a warning indication module operable to provide a warning indication if the selected one or more patient temperature regulation tools are incompatible with the inputted type of medical procedure.

The application may further comprise a recommendation module operable to identify recommended patient temperature regulation tools which are compatible with the inputted type of medical procedure.

The database preferably includes an update module which allows a user to update the database with one or more properties of additional patient temperature regulation tools.

Although the computer system may consist of a standalone computer, the computer system typically comprises a server computer in data communication with a client computer.

Preferably the server comprises: the database; the input module; the indication module; and the visual aid module.

Preferably, the client comprises the interface module.

Either the client or the server may comprise the calculation module.

In one embodiment the client comprises the calculation module. In an alternative embodiment the server comprises the calculation module.

Typically, the interface module receives the estimated patient heat balance and the visual aid from the calculation and visual aid modules respectively.

Preferably the interface module is a graphical user interface module.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
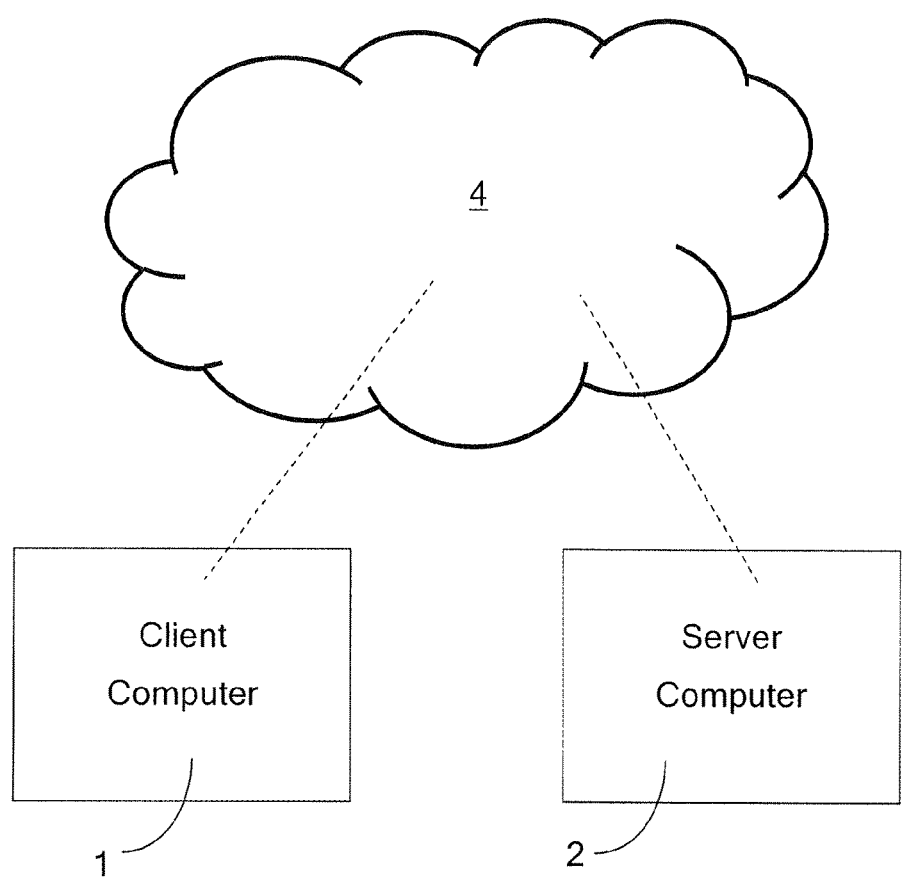
FIG. 1 is a block diagram illustrating a client computer communicating with a server computer over a data communications network.

FIG. 1 is a block diagram illustrating a client computer 1 communicating with a server computer 2 over a data communications network 4 (such as the Internet, a Local Area Network or a Wide Area Network). The server computer 2 runs an application 5 which can be accessed via the network 4 by a web browser running on the client computer 1. The web browser provides a graphical user interface module through which web pages supplied by the server computer 2 may be displayed, and inputs to the application can be submitted.

Figure 2:
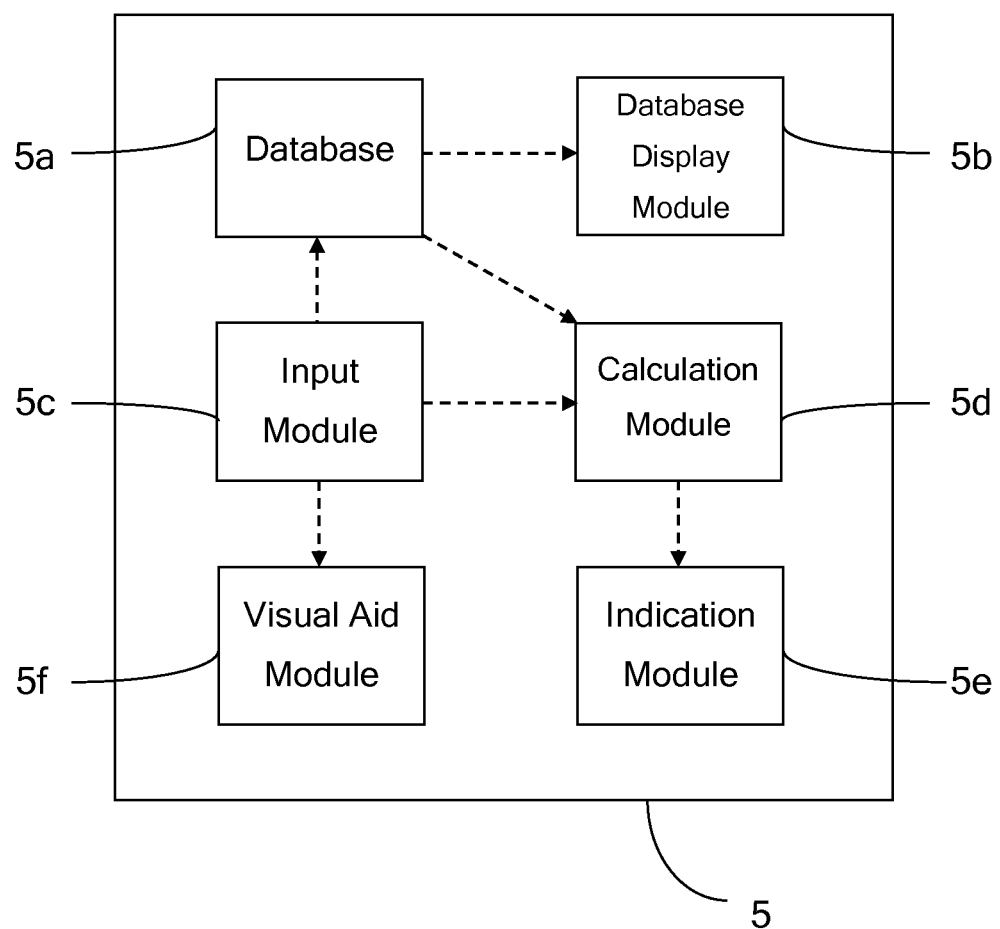
FIG. 2 is a block diagram illustrating various features of an application for selecting one or more patient temperature regulation tools.

The application running on the server computer 2 is designed to enable a user to select one or more patient temperature regulation tools which are suitable for regulating the heat balance of a patient undergoing a medical procedure. As shown in FIG. 2, the application 5 comprises a database 5a which stores one or more properties (preferably including one or more thermal properties) of each of a plurality of patient temperature regulation tools and a database display module 5b which is operable to provide a visual indication of each of the plurality of patient temperature regulation tools stored in the database. The application further comprises an input module 5c which is operable to receive a selection of one or more of the patient temperature regulation tools displayed by the database display module 5b. The input module 5c may also be operable to receive an input of: one or more patient parameters; one or more environmental conditions relating to an environment in which the medical procedure will take place; a type of medical procedure; and/or other variables such as a type of anaesthetic or parameters relating to a surgical wound. A calculation module 5d is provided for calculating an estimated heat balance of a patient, taking into account one or more properties of the selected patient temperature regulation tools, said properties being obtained from the database 5a. An indication module 5*e* is operable to receive the estimated patient heat balance calculated by the calculation module 5*d* and to provide an indication of that estimated patient heat balance which can be understood by a user. The application 5 further comprises a visual aid module 5*f* which is operable to provide a visual aid to a user which illustrates the one or more selected patient temperature regulation tools regulating the temperature of a patient. This is explained in more detail below.

It will be understood that one or more modules of the application running on the server 2 could alternatively be implemented on the client computer 1. For example, the calculation module 5*d* may be provided at the client computer 1, in which case the results of the estimated heat balance may be calculated at the client computer. The calculated estimated heat balance may then be transmitted to the server 2 by the client 1 to be included on a web page which is generated by the server 2 (the web page being subsequently transmitted to and displayed by the web browser running on the client 1). Alternatively, the estimated heat balance may be provided on a separate local display generated by the client computer 1.

It will also be understood that the application may alternatively be implemented on a standalone computer, the user providing inputs to and observing outputs from the application on said standalone computer. However, in the description below, it will be assumed that all of the modules of the application shown in FIG. 2 are implemented on the server 2 with the graphical user interface module being implemented at the client.

Figure 3:
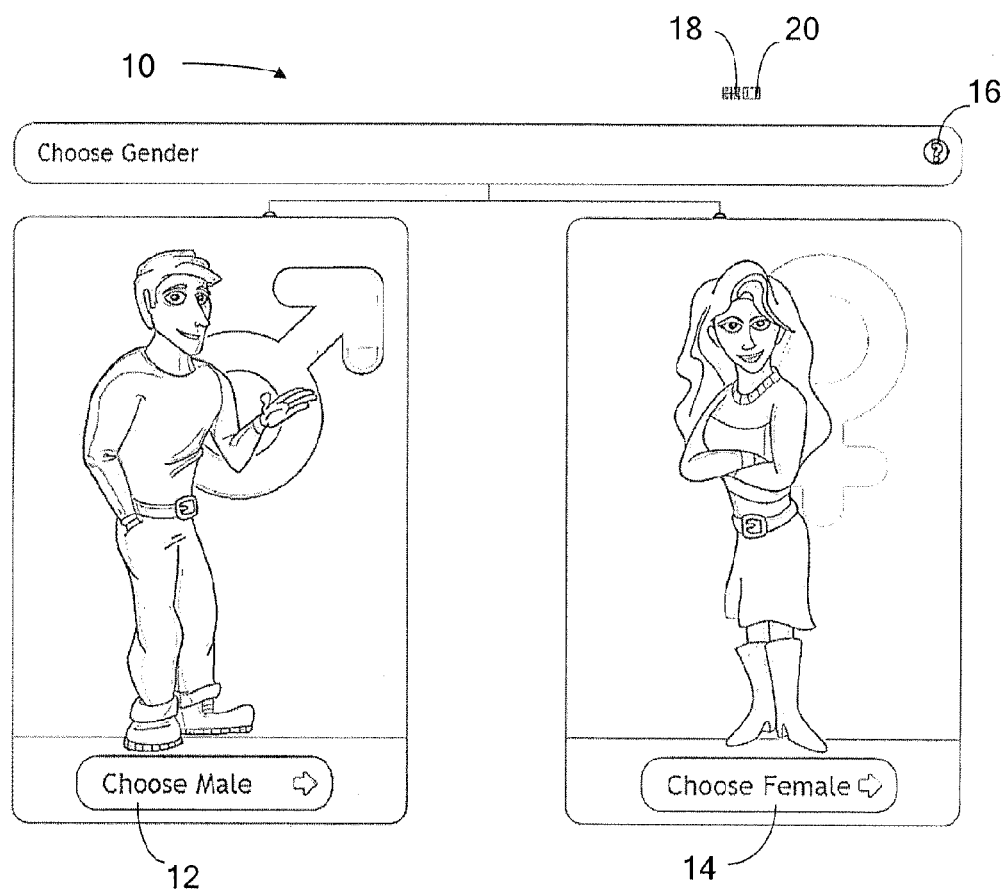
FIG. 3 shows a home page of the application of FIG. 2 where the gender of a patient may be selected and transmitted to the application running on the server.

When a user accesses the application initially via the browser running on the client computer 1, a "home page" 10, illustrated in FIG. 3, is displayed. The home page 10 comprises a pair of buttons 12, 14 by which a user can select the gender of a (real or fictional) patient who is to undergo a medical procedure. The buttons 12, 14 form part of the input module of the application. If button 12 is selected, the application is provided with an input parameter indicating that the patient is male; if button 14 is selected, the application is provided with an input parameter indicating that the patient is female. A help facility can be accessed by selecting "help" button 16, while the language of the text on the web page can be changed by selecting a relevant flag 18, 20.

Figure 4:
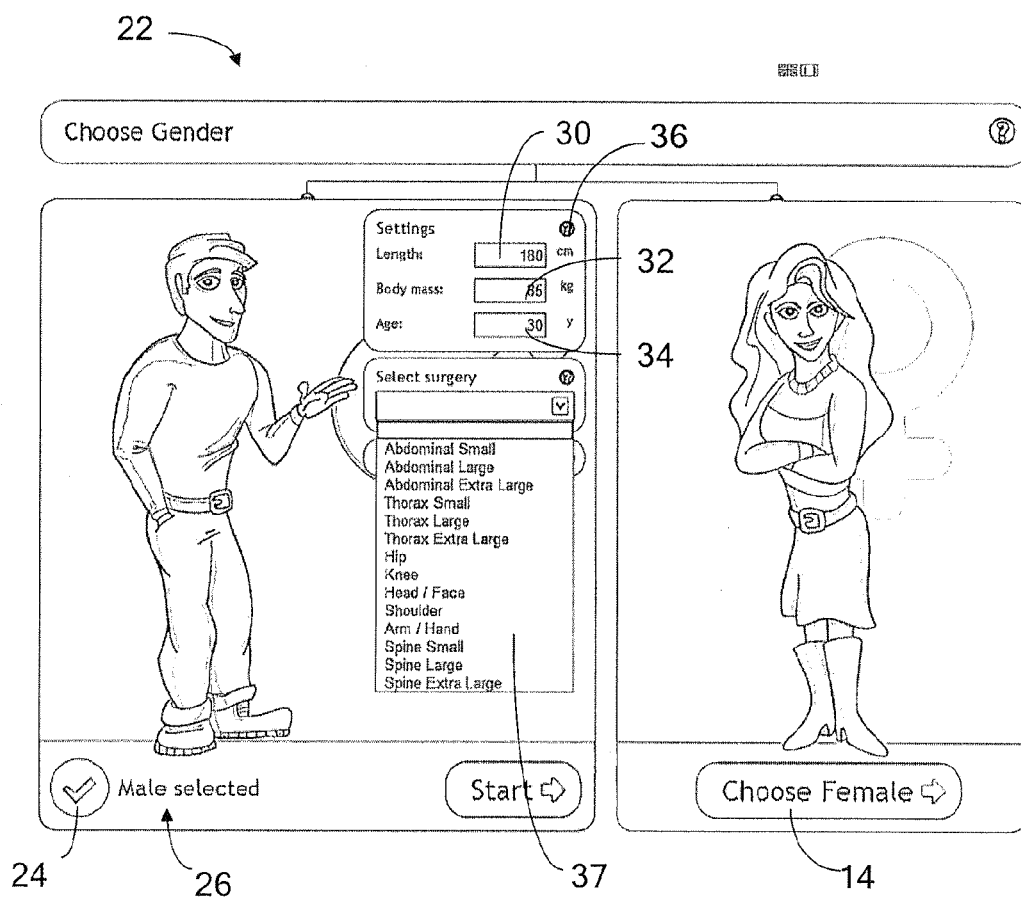
FIG. 4 shows a web-page provided by the application of FIG. 2 which provides input fields for entering one or more patient parameters and a type of medical procedure.

After the gender of the patient has been selected, the web browser is sent a new page 22, illustrated in FIG. 4, by the application 5 running on server 2. It can be seen from the illustrated example that the user has selected "male" on the previous page as indicated by the "tick" graphic 24 and "Male selected" caption 26 on the bottom left corner of page 22.

On page 22, a plurality of patient parameters may be input by the user. For example, the height of the patient may be entered in a first input box 30, the body mass of the patient may be entered in a second input box 32, and the age of the patient may be entered at a third input box 34. The first, second and third input boxes 30-34 also form part of the application's input module 5*c*. When the parameters are entered to the input boxes 30-34, they are submitted to the calculation module 5*d* of the application. A help facility may be accessed at any time by selecting the help icon 36.

A type of medical procedure may be selected from a list 37 of possible medical procedures which also forms part of the application's input module 5*c*. The type of medical procedure may simply indicate an internal or external patient body part which is the subject of the procedure. Additionally or alternatively, the type of medical procedure may provide a relative size from which the application 5 may estimate an exposed surface area of the patient required for the procedure (see below). For example, in FIG. 4, the list from which the type of medical/surgical procedure is selected lists the following body parts: abdominal small, abdominal large, abdominal extra large, thorax small, thorax large, thorax extra large, hip, knee, head/face, shoulder, arm/hand, spine small, spine large, spine extra large. When a type of medical procedure has been selected, an indication of the selection is submitted to the calculation module 5*d* of the application 5.

If the user has inadvertently selected the wrong gender on home page 10, the user may alternatively select the "choose female" button 14 which is also provided on page 22.

Figure 5:
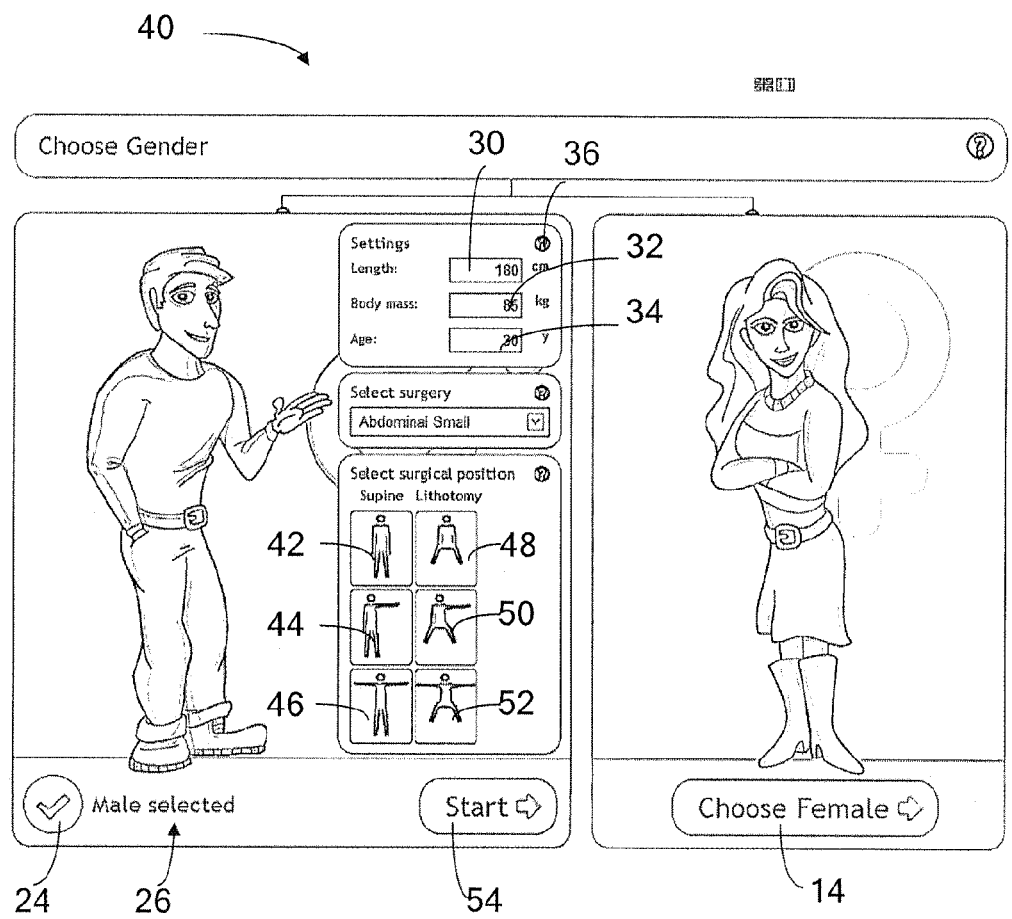
FIG. 5 shows a web-page provided by the application of FIG. 2 which provides an input field for a surgical position which a patient may need to adopt during a medical procedure.

After the user has input the patient parameters and selected a type of medical procedure, a new page 40 is displayed on the browser as shown in FIG. 5. Page 40 displays the caption 26 indicating that "male" gender has been selected, the selected type of medical procedure (in this example "abdominal small") in place of list 37 and the patient parameters input on page 22. Page 40 also provides a plurality of graphics 42-52 each providing a particular choice of surgical position which the patient may be required to adopt during the medical procedure. The user may select a surgical position by selecting the graphic associated with the chosen position. The graphics 42-52 thus also form part of the application's input module 5*c*. It will be understood that the patient's surgical position may alternatively be determined by the inputted type of medical procedure.

Figure 6:
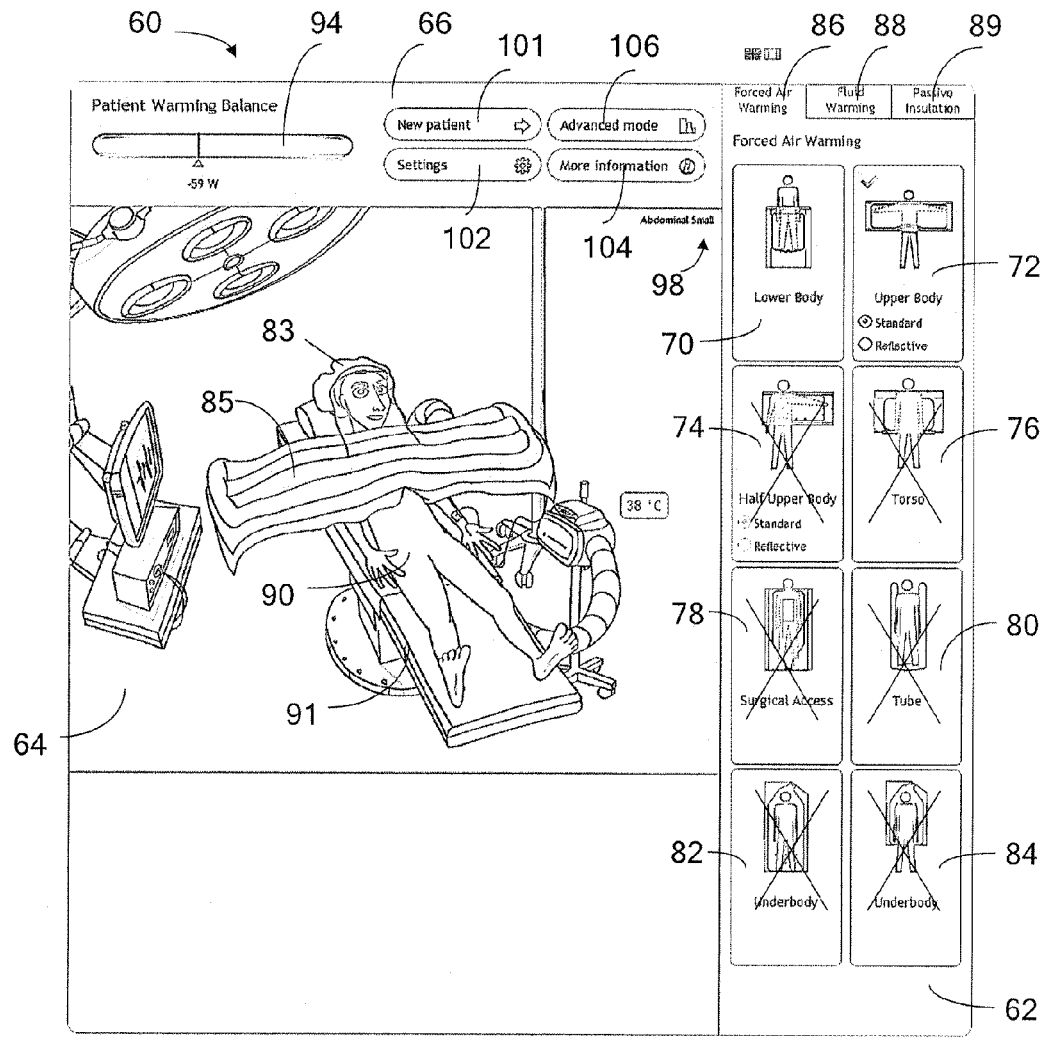
FIG. 6 shows a web-page provided by the application of FIG. 2 which comprises frames for selecting one or more temperature regulation tools, displaying a visual aid and displaying a visual indication of a calculated estimate of a patient warming balance.

When the user has selected on the chosen icon 42-52, a new page 60 shown in FIG. 6 may be displayed. Any of the selections or inputs provided on pages 10, 22 or 40 may be skipped by selecting the "start" button 54 at any time. Additionally it may be necessary to select the "start" button 54 after selecting a chosen surgical position to prompt the application to provide new page 60.

Page 60 comprises three frames 62, 64, 66. On a first frame 62, which forms part of the application's input module, a user can select one or more patient temperature regulation tools 70-84 which may be used to regulate the heat balance of the patient undergoing the medical procedure. Three tabs 86-89 are provided on frame 62, each tab grouping together a plurality of patient temperature regulation tools of a given type. For example, tab 86 comprises patient regulation tools of a "Forced Air Warming" type—that is, in use, the tools displayed under tab 86 are intended to heat a patient by using forced heated air. Tab 88 comprises patient temperature regulation tools of a "Fluid Warming" type—that is, in use, the tools displayed under tab 88 are intended to heat a patient by providing heated fluid (e.g. blood) which is injected into the patient's body. Tab 89 comprises patient temperature regulation tools of a "Passive Insulation" type—that is, in use, the tools displayed under tab 89 are intended to heat a patient by passively insulating some or all of the patient's body. Buttons are associated with each tab 86-89. When the button associated with one of the tabs 86-89 is selected, the tools grouped under that tab are displayed in frame 62.

As shown in FIG. 6, each tool 70-84 is represented by a graphic which illustrates how that tool is intended to interact with a patient, and typically further provides a caption confirming what is illustrated by the graphic. For example, tool 70, which is a lower body heating tool of the "Forced Air Warming" type, is represented by a graphic illustrating a generic patient wearing a forced air warming tool around his/her lower body. In addition the caption "Lower Body" is provided, and it is clear from the heading "Forced Air Warming" in the frame 62 that tool 70 is of the "Forced Air Warming" type. This provides a user-friendly, easy-to-use selection means by which a user can select one or more tools for regulating the heat balance of a patient.

Preferably, the graphics illustrating the tools 70-84 also illustrate an orientation of the patient when the tool represented by that graphic is in use. For example, the graphic representing tool 72 shows the patient with his/her arms outstretched, whereas the graphic representing tool 74 shows the patient with only one arm outstretched. The graphic 80 shows the patient with both arms by his/her side. Such orientation information may also be provided by the database 5a and used to filter which of the patient temperature regulation tools may be selected—for example, those tools which are incompatible with an input surgical position may be excluded from selection.

Figure 7:
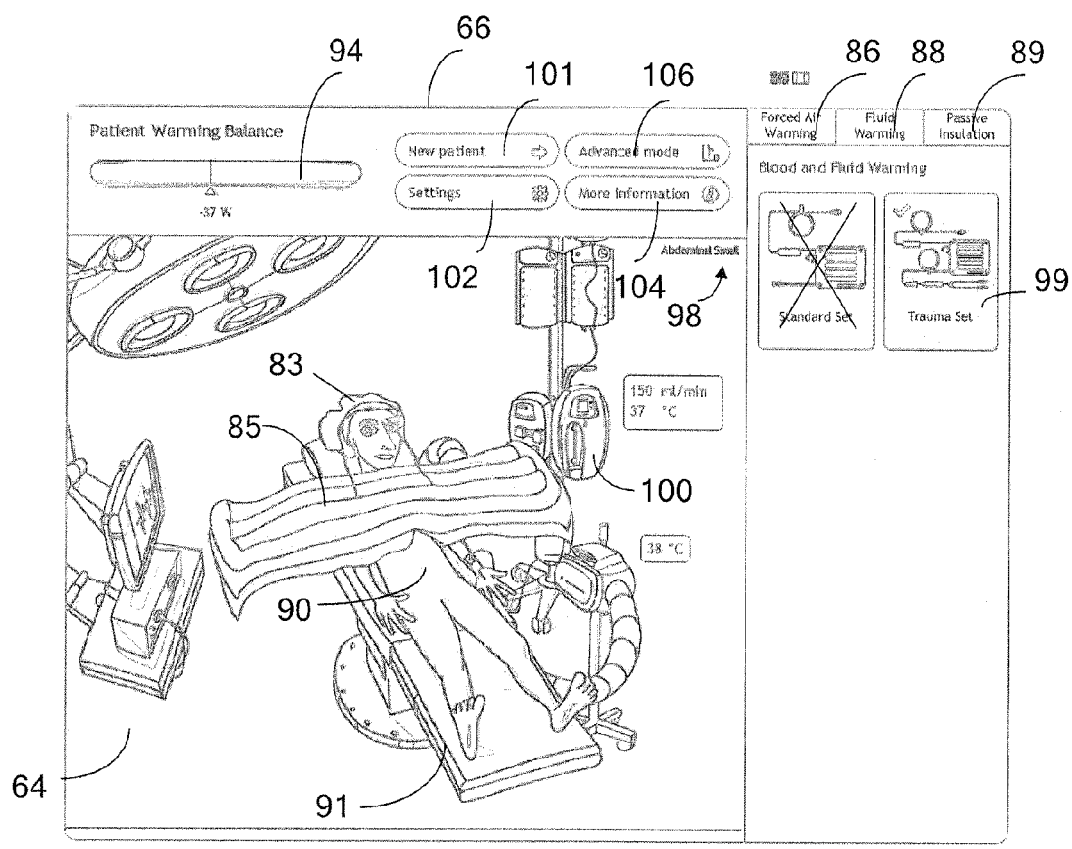
FIG. 7 shows a web-page provided by the application of FIG. 2 similar to that of FIG. 6 but wherein the selection of a temperature regulation tool of the "Fluid Warming" type is shown, the visual aid illustrating all of the selected temperature regulation tools together in the act of regulating the temperature of the patient.

Although not shown in FIGS. 6, 7, the graphics 70-84 may also display one or more thermal properties concerning the tools they represent. This provides further information to the user, allowing him/her to make a more informed judgement as to whether a particular tool is suitable for a particular patient and/or a particular medical procedure before the tool is selected.

As also shown in FIG. 6, the graphics 70-84 may comprise a plurality of radio buttons to indicate the selection of one of a plurality of versions of a given tool which may have different properties. For example, tools 72, 74 may be "Standard" or "Reflective". By selecting the appropriate radio button, the user can select a particular one of these tools.

The tools represented on frame 62 comprise some or all of the tools, one or more properties of which are stored on the database stored in memory 6 of the server computer 2. Thus, frame 62 of page 60 provided by the server computer also provides the database display module operable to provide a visual indication of each of the plurality of temperature regulation tools stored in the database. Typically, taking the tools under all of the tabs 86-89 together, all of the tools one or more properties of which are stored in the database may be displayed on page 62.

A single tool from a single tab may be selected. Alternatively a single tool from each of a plurality of tabs may be selected, a plurality of tools may be selected from a single tab, or one or more tools may be selected from each of a plurality of tabs.

It will also be understood that any method of inputting the type of medical procedure or patient parameters or selecting the one or more patient temperature regulation tools may be employed by the input module 5c.

Optionally, the application may further comprise a "warning module" which provides a warning if the selected tool(s) is/are incompatible with the patient parameters entered, with the inputted medical procedure type and/or with another selected tool.

Such a warning may be, for example an audio alert but more typically the alert is a visual alert.

Optionally, the application may further comprise a "recommendation module" which provides a recommendation of one or more of the patient temperature regulation tools from the database 5a, the recommended tools being compatible with the patient parameters and/or medical procedure and/or other selected patient temperature regulation tools. Preferably, those tools which are not recommended may be excluded from selection, either by disabling the buttons associated with those tools on the page provided by server 2 or by not displaying the tools in frame 62.

Figure 8:
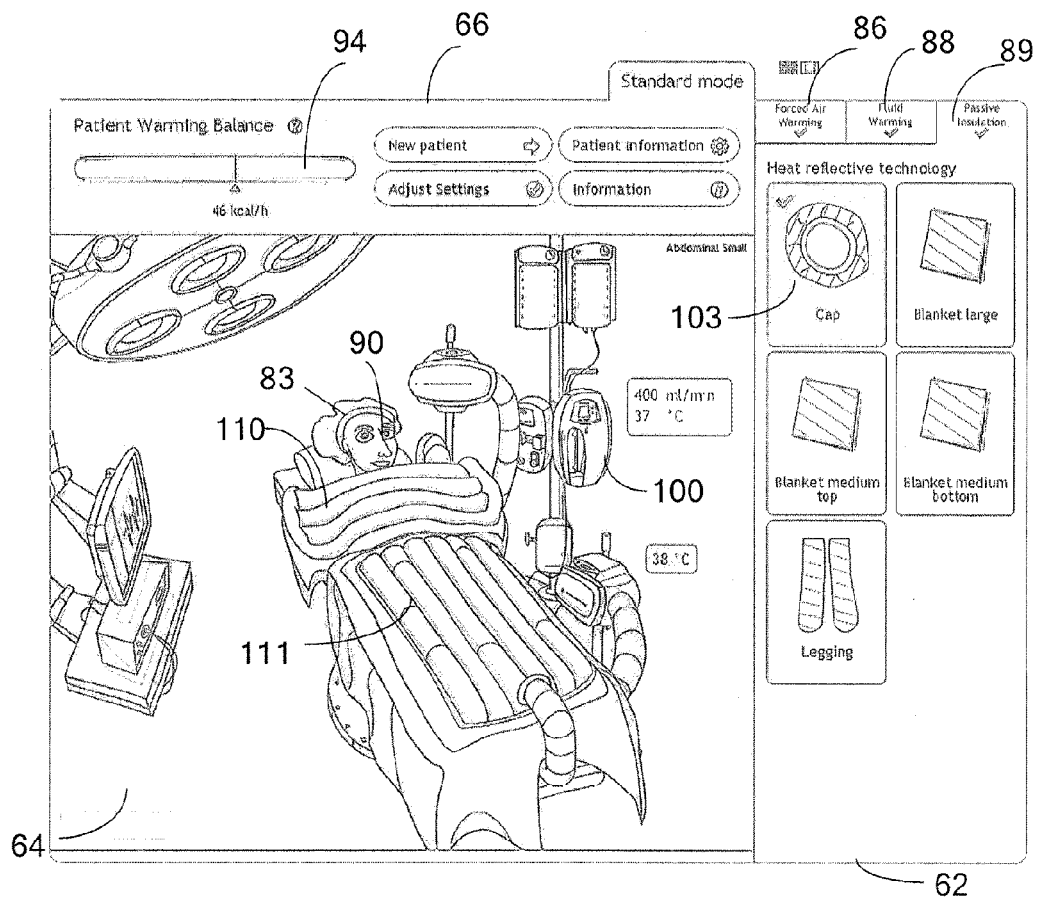
FIG. 8 shows a web-page provided by the application of FIG. 2 similar to that of FIGS. 6 and 7 but wherein the visual aid illustrates an alternative combination of selected patient temperature regulation tools together in the act of regulating the temperature of the patient.
Figure 9:
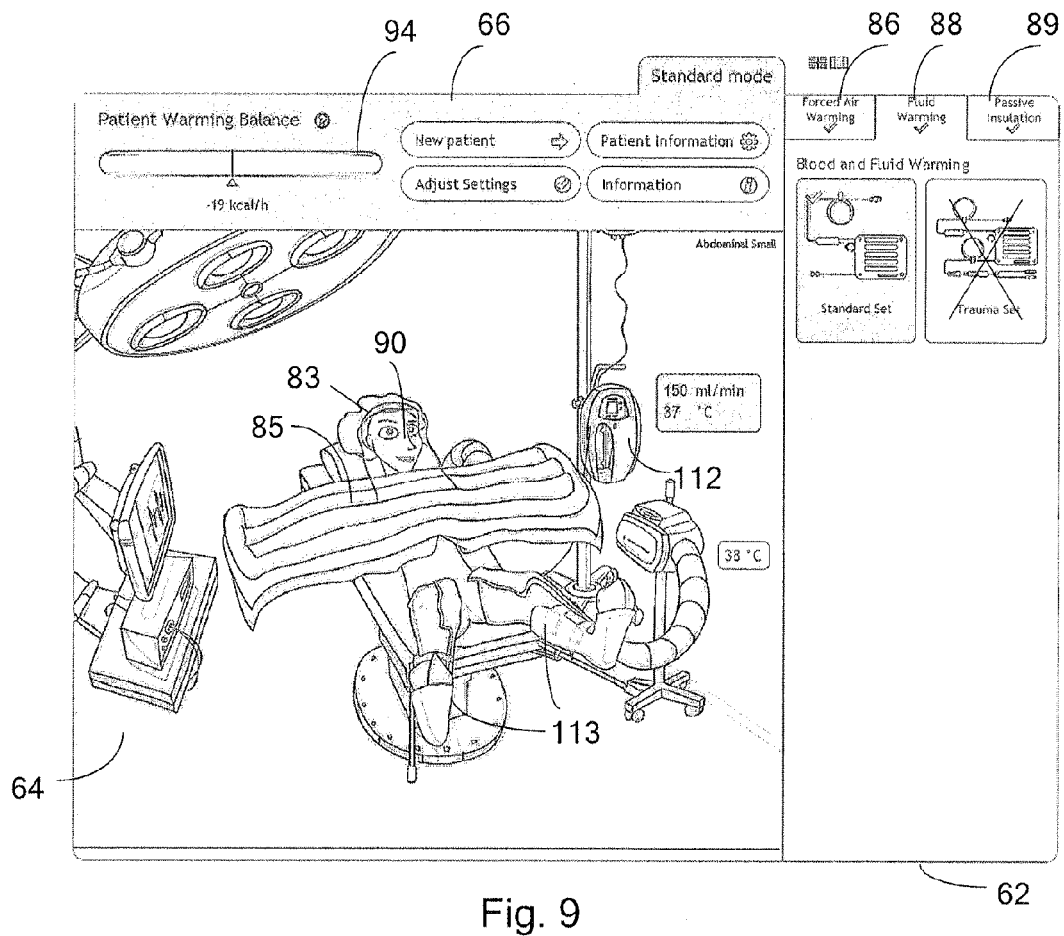
FIG. 9 shows a web-page provided by the application of FIG. 2 similar to that of FIGS. 7-8, but wherein the visual aid illustrates another alternative combination of selected patient temperature regulation tools together in the act of regulating the temperature of the patient.

In the examples of FIGS. 6-9, the recommendation module operates by displaying a cross (X) on, and disabling, the buttons representing tools which are not recommended for use with the other tools that are selected. For example, in FIG. 6, the upper body tool of the "Forced Air Warming" type has been selected and the only other tool of this type that is compatible with the upper body tool is the lower body tool 70; all other tools of the "Forced Air Warming" type 74-84 provided are not recommended for use with the upper body tool because they would overlap with the upper body tool. Therefore, the tools represented by graphics 74-84 are crossed out and their selection is disabled. Similarly, in FIG. 7 the standard and trauma sets of blood warming tools are not recommended for use together. The trauma set is selected, so the standard set is crossed out and its selection is disabled. The opposite situation is shown in FIG. 9. Note that the cap selected in FIG. 8 is compatible with any other tool of the "Passive Insulation" type. Accordingly, none of the other tools of this type shown in FIG. 8 are excluded from selection when the cap is selected.

Although crosses are used to indicate an excluded or non-recommended tool, it will be understood that any suitable indication may be provided. For example those tools that are excluded from selection may be "greyed out" (or even not displayed at all) or an audible warning signal may be played if a user tries to click on an excluded tool. An excluded tool can of course be re-instated for selection by deselecting the tool(s) with which it is incompatible.

Second frame 64 forms part of the visual aid module 5e of the application 5 which, as explained above, is operable to provide a visual aid illustrating the one or more selected patient temperature regulation tools regulating the temperature of a patient.

The visual aid is provided in response to the selection of the one or more tools 70-84 on frame 62. The patient is represented by a visual representation 90 which is preferably illustrated in the surgical position selected by the user on page 40 (see FIG. 4) on a surgical bed 91 (where appropriate). The visual aid also shows the one or more selected patient temperature regulation tools in the act of regulating the patient's temperature. In the example shown on FIG. 6, the user has selected the standard upper body tool 72 of the "Forced Air Warming" type (as shown by the "tick" graphic 92 shown in the top left hand corner of the graphic representing tool 72), a representation 85 of which is shown installed on the visual representation 90 of the patient by the visual aid in frame 64. Frame 64 may also optionally show surgical equipment unrelated to the heating of the patient in order to provide a more convincing overall impression of a medical/surgical environment.

Third frame 66 provides a visual indication 94 (in the form of a slide bar having a sliding indicator together with a caption indicating numerical value of the estimated heat balance in the illustrated embodiment) of an estimated patient heat balance calculated by the calculation module 5d. Whether a patient's heat balance is at equilibrium (no net heat gain or heat loss), positive (heat gain) or negative (heat loss) depends on the amount of heat generated by the body, the amount of heat provided to the body and the heat lost from the body.

Many different factors influence a patient's heat balance, including the patient's gender, mass, age, height, average skin temperature, environmental conditions of operating theatre (such as ambient temperature and pressure, relative humidity, velocity of air flow), surface area of the patient's wound/exposed organs during the procedure, volume flow and temperature of supplied IV-fluids, volume and temperature of supplied fluids to body surface (such as alcohol/iodine), volume flow and temperature of supplied gases to the patient and so on.

A patient's heat balance may be expressed as a sum of heat flows with respect to the patient's body:

$$q_{patient} = q_{metabolic} + q_{uncovered} + q_{passive\_insulated} + q_{active\_warmed} + q_{IV\_fluids} + q_{surgical_{wound}}$$

where:
- $q_{patient}$ is the overall heat flow of the patient (W)
- $q_{metabolic}$ is the metabolic heat flow of the patient (W)
- $q_{uncovered}$ is the heat of uncovered body parts (W)
- $q_{passive\_insulated}$ is the heat flow of passively insulated body parts (W)
- $q_{active\_warmed}$ is the heat flow of actively warmed body parts (W)
- $q_{IV\_fluids}$ is the heat flow of supplied intravenous fluids (W)
- $q_{surgical\_wound}$ is the heat flow of any surgical wounds (W)

Each of these heat flows will be discussed in more detail below.

Metabolic Heat Flow

Metabolism is typically the only internal source of heat in the human body. Body tissues produce heat in proportion to their metabolic rates. The metabolic heat rate can be estimated using the Katch McArdle formula:

$$BMR = 17.93 + (1.05 * LBM)$$

where:
- BMR = Basal Metabolic Rate (W)
- LBM = Lean Body Mass (kg)

The lean body mass is calculated differently for men and women:

$$LBM_{(men)} = 1.10 * m - \frac{128 * m^2}{(100 * l)^2}$$

$$LBM_{(women)} = 1.07 * m - \frac{148 * m^2}{(100 * l)^2}$$

where in both cases:
- LBM is the lean body mass (kg);
- m is the body mass (kg); and
- l is the body length (m), i.e. height of patient Induction of general anaesthesia is responsible for a 20-30% reduction in metabolic heat production. Furthermore, the basal metabolic rate increases with a factor of 2 for each 10° C. increase of tissue temperature.

Accordingly, the metabolic heat flows for men and women respectively can be calculated by the calculation module 5d as follows:

$$q_{metabolic(men)} = r.f. * \left(17.93 + \left(1.05 * \left(1.10 * m - \frac{128 * m^2}{(100 * l)^2}\right)\right)\right) e^{0.0693*(T_{core}-36.9)}$$

$$q_{metabolic(women)} = r.f. * \left(17.93 + \left(1.05 * \left(1.07 * m - \frac{148 * m^2}{(100 * l)^2}\right)\right)\right) e^{0.0693*(T_{core}-36.9)}$$

where:
- r.f. is a reduction factor of metabolic heat production dependent on anaesthesia; and
- $T_{core}$ is the core temperature of the patient (° C.)
- Other parameters are as defined above.

The core temperature of the patient and the reduction factor may be estimated by the calculation module 5d. Alternatively, another input field for receiving the core temperature of the patient may be provided. The mass and height of the patient are typically provided (as explained above) as inputs; however, these parameters may alternatively be allocated default values if they are not provided by the user.

Heat Flow of Uncovered Body Parts

The main heat transfer mechanisms of uncovered body parts are radiation, convection and evaporation. For environments without active air displacement the convection is referred to as natural convection (driven by temperature differences in air). For environments with active air displacement the convection is referred to as forced convection.

A mathematical expression for the heat flow of uncovered body parts is as follows:

$$q_{uncovered} = A_{uncovered} * q'_{uncovered}$$

where
- $A_{uncovered}$ is the surface area of uncovered body parts (m²); and
- $q'_{uncovered}$ is the heat flux of uncovered body parts (W/m²).

The average surface area of uncovered body parts may be estimated using the relationship provided below (under heading "Surface Areas"). For use in this calculation, the medical procedure type may determine a surface area $A_{mattress\_contact}$ which estimates a surface area of the patient's body which contacts the mattress of the surgical bed during the medical procedure and/or an indication of whether the medical procedure will be conducted on a small, large or extra large portion of a body part.

The heat flux of uncovered body parts, $q'_{uncovered}$ is calculated by the calculation module 5d as follows:

$$q'_{uncovered} = -\left(\begin{array}{l} 3 \cdot \sqrt[4]{t_{avg\_skin\_uncov} - T_{amb}} \cdot (T_{avg\_skin\_uncov} - T_{amb}) + \\ 5.67 \cdot 10^{-8} \cdot 0.98 \cdot ((T_{avg\_skin\_uncov} + 273)^4 - (T_{amb} + 273)^4 + \\ 2430 \cdot 1.2706 \cdot 10^{-6} \cdot ((133.32 \cdot (1.92 \cdot T_{avg_{skin_{uncov}}} - 25.3)) - \\ \left(610.78 \cdot e^{\left(\frac{T_{amb}}{T_{amb}+238.3}17.2694\right)} \cdot rh\right) \end{array}\right)$$

where
- $T_{avg\_skin\_uncov}$ is average uncovered skin temperature (° C.)
- $T_{amb}$ is ambient temperature (° C.)
- rh is relative humidity Typically, the uncovered skin temperature $T_{avg\_skip\_uncov}$ is set to 28° C. However, an input field may be provided to enable this parameter to be changed.

Heat Flow of Passively Insulated Body Parts

With passive insulators (such as surgical drapes, duvets and space blankets), the heat flow from skin is reduced. Heat loss by evaporation is less than that for uncovered skin because the environment between the skin and the insulator will reach a relative humidity near 100%. The model employed by the calculation module 5d assumes that there is no evaporative heat loss. In one embodiment, the calculation module determines the heat flow of passively insulated body parts as follows:

$$q_{passive\_insulated} = A_{passive\_insulated} * q'_{passive\_insulated}$$

where:
- $A_{passive\_insulated}$ is the surface area of passively insulated body parts;
- $q'_{passive\_insulated}$ is the heat flux of passively insulated body parts The heat flux, $q'_{passive\_insulated}$, may be calculated by the calculation module 5d as follows:

$$q'_{passive\_insulated} = -i.f. \cdot \begin{pmatrix} 3 \cdot \sqrt[4]{T_{avg\_skin\_pass} - T_{amb}} \cdot (T_{avg\_skin\_pass} - T_{amb}) + \\ 5.67 \cdot 10^{-8} \cdot 0.98 \cdot ((T_{avg\_pass} + 273)^4 - T_{amb} + 273)^4) \end{pmatrix}$$

where:
- i.f. is an insulation factor of the selected passive insulation tools provided by the database;
- $T_{ave\_skin\_pass}$ is the average passive insulated skin temperature;
- $T_{amb}$ is the ambient temperature of the operating theatre;

The average passive insulated skin temperature may be estimated by the calculation module. Alternatively, an input field may be provided by the input module 5c of the application which is operable to receive an input estimate of the average passive insulated skin temperature which is passed to the calculation module 5d.

Heat Flow of Actively Heated Body Parts

Actively warmed body parts receive heat (or heat is extracted from the body parts if the air temperature is lower than the skin temperature) by convection and radiation from a forced air warming blanket or garment. At the same time, heat is extracted from the skin by evaporation. The heat flow of actively warmed body parts may be calculated by the calculation module 5d as follows:

$$q_{active\_warmed} = \begin{pmatrix} \alpha \cdot A_{active_{warmed}} \cdot (T_{air} - T_{avg skin_{active}}) - \\ A_{active\_warmed} \cdot 2430 \cdot 1.2706 \cdot 10^{-6} \cdot \\ \left( (133.32 \cdot (1.92 \cdot T_{avg\_skin\_active} - 25.3)) - \left( 610.78 \cdot e^{\left(\frac{T_{air}}{T_{air}+238.3} 17.2694\right)} \right) \right) \end{pmatrix}$$

where:
- $\alpha$ is the heat transfer coefficient from the active heating tool to the patient's skin (W/m²K);
- $A_{active\_warmed}$ is the surface area of actively warmed body parts (m²);
- $T_{air}$ is the average forced air temperature that blows over the skin (° C.);
- $T_{avg\_skin\_active}$ is the average skin temperature of the actively warmed skin (° C.)

The surface area of active warmed body parts may be estimated by the calculation module 5d from the selection of tools 70-84 and/or from the inputted medical procedure type. Alternatively, default values may be stored in the database and provided to the calculation module. As another alternative, an input field may be provided which is operable to receive an estimation of the surface area of the actively warmed body parts.

The heat transfer coefficient is typically provided to the calculation module from the database. The average forced air temperature is typically provided to the calculation module 5d from the database 5a.

The average skin temperature of the actively warmed skin may be estimated by the calculation module, provided to the calculation module by the database or input via an additional input field by a user.

Heat Flow of a Surgical Wound

The heat flow of a surgical wound typically consists of evaporation, convection and radiation. The calculation module 5d may assume that the surface of the surgical wound has the body core temperature, and that the surface of the wound is wet. Accordingly, the heat flow of the surgical wound may be calculated by the calculation module 5d as follows:

$$q_{surgical\_wound} = -A_{surgical\_wound} \cdot \begin{pmatrix} 2270 \cdot 1000 \cdot (25 + 19 \cdot v_{air})/3600 \cdot (s.h.r - h.r) + \\ 3 \cdot \sqrt[4]{T_{core} - T_{amb}} \cdot (T_{core} - T_{amb}) + \\ 5.67 \cdot 10^{-8} \cdot 0.98 \cdot ((T_{core} + 273)^4 - (T_{amb} + 273)^4) \end{pmatrix}$$

where:

$$s.h.r. = \frac{0.62198 \cdot Ps}{(P_{amb} - Ps)}$$

$$Ps = \frac{e^{77.345 + 0.0057 \cdot (T_{core}+273) \frac{7235}{T_{core}+273}}}{(T_{core} + 273)^{8.2}}$$

$$h.r = 0.0010057 \cdot \frac{T_{amb}}{35} \cdot T_{amb} \cdot r.h$$

and where:
- $A_{surgical\_wound}$=surface area of surgical wound (m²)
- $V_{air}$=velocity of ambient air (down flow) (m/s)
- s.h.r=specific humidity ratio at saturation (–)
- h.r=humidity ratio (–)
- $T_{core}$=core temperature (° C.)
- $T_{amb}$=ambient temperature (° C.)
- Ps=Saturation pressure of water vapour (Pa)
- r.h=relative humidity (–)

The surface area of the surgical wound, $A_{surgical\_wound}$, velocity of ambient air, $V_{air}$, specific humidity ratio at saturation, s.h.r., humidity ratio, h.r., core temperature, $T_{core}$, ambient temperature $T_{amb}$, saturation pressure of water vapour, Ps, and relative humidity, r.h. may be estimated by the calculation module 5d, provided to the calculation module from the database 5a, or input to the application via an additional input field by a user.

Heat Flow of Supplied Intravenous (IV) Fluids

The heat flow of supplied IV-fluids depends on the mass flow of fluid to the body, the specific heat capacity of the fluid and the temperature of the fluid fed to the body. This can be determined by the following equation:

$$q_{IV-fluids} = q_{vol-fluid} \cdot 10^{-6} \cdot \frac{1}{60} \cdot \rho_{fluid} \cdot c_{p-fluid} \cdot (T_{fluid} - T_{core})$$

where:
- $q_{IV\_fluids}$=heat flow of IV fluids (W)
- $q_{vol\_fluid}$=volume of fluids (ml/min)
- $\rho_{fluid}$=density of fluid (kg/M²)
- $c_{p\_fluid}$=specific heat capacity of fluid (J/kgK)
- $T_{fluid}$=fluid temperature at the end of IV-line connected to patient (° C.)
- $T_{core}$=core temperature of patient (° C.)

Typical specific heat capacities and densities of exemplary fluids which may be injected into the patient are as follows:

| Fluid | Specific Heat Capacity [J/kg · K] | Denisty [kg/m³] |
|---|---|---|
| Water | 4182 | 998 |
| Blood Plasma (Hct = 0%) | 4151 | 1025 |
| Whole Blood (Hct = 40%) | 4011 | 1050 |

A total surface area, $A_{body\_surface}$ of the patient's body can be calculated as follows:

$$A_{body\_surface} = m^{0.425} * (1*100)^{0.725} * 0.007184$$

where m is the mass of the body (kg)

l is the length (height) of the body (m)

As described above, the calculation module 5d typically uses the following surface areas:

$A_{uncovered}$ (the surface area of uncovered skin on patient's body)

$A_{passive\_insulated}$ (the surface area of passively insulated skin)

$A_{actively\_warmed}$ (the surface area of actively warmed skin)

$A_{mattress\_contact}$ (the surface area of skin expected to contact the mattress of the surgical bed during the medical procedure)

$A_{surgical\_wound}$ (the surface area of any surgical wounds)

Accordingly, the calculation module 5d may work under the assumption that the total body surface area, $A_{body\_surface}$ is equal to the sum of these surface areas:

$$A_{body\_surface} = A_{uncovered} + A_{passive\_insulated} + A_{actively\_warmed} + A_{mattress\_contact} + A_{surgical\_wound}$$

Thus, if the calculation module 5d has access to (e.g. if stored in the database or entered by a user), or can estimate five out of the above six variables, the remaining surface area can be readily calculated.

Net Heat Balance

Each discrete contribution to the net heat balance of a patient can thus be calculated by the calculation module 5d typically by using input parameters and one or more thermal properties of the selected tools provided from the database 5a. By summing the discrete contributions to the overall patient heat balance, a final heat balance figure can be calculated and a visual indication displayed on frame 66 of page 60.

As described above, in the illustrated embodiment of FIGS. 6 and 7, the visual indication comprises a slide bar with a sliding indicator together with a caption indicating numerical value of the estimated heat balance. However, it will be understood that any appropriate alternative visual indication may be provided, such as an alphanumeric display or a colour coded chart. It will also be understood that the indication of the heat balance is not necessarily visual. For example, an audio (e.g. speech) message may be provided to indicate the heat balance value.

Discussion

In FIG. 6, the standard upper body tool of the "Forced Air Warming" type is selected (see frame 62), as is the cap tool of the "Passive Insulation" type (shown in the visual indication of frame 64). The visual aid in frame 64 provides representations 83, 85 of the cap and standard upper body tools respectively, together in the act of regulating the patient's temperature. The calculation module estimates that the present selection of tools provides the patient with a patient warming balance of −59 W. Accordingly, if only these tools are used to regulate the heat balance of a patient during the selected "Abdominal small" procedure (see caption 98 in FIG. 6), the patient would suffer a net heat loss.

Additional patient temperature regulation tools may be selected to provide the required heat balance. For example, as shown in FIG. 7, the standard upper body tool 72 under the "Forced Air Warming" tab, the trauma set blood tool 99 under the "Fluid Warming" tab and the Cap tool 103 (see FIG. 8) under the "Passive Insulation" tab are selected. Accordingly, representations 83, 85, 100 of the cap tool, standard upper body tool and trauma set tool are shown by the visual aid together in the act of regulating the temperature the patient. As shown on the indicator 94 in frame 66 of FIG. 7, the patient heat balance, taking into account contributions from all presently selected tools (cap, standard upper body, trauma set), is −37 W, which is an improvement on the −59 W value achieved with only the standard upper body and cap tools.

It will be understood that the indication of heat balance may be provided in any suitable units (see FIGS. 8, 9 where instead of Watts, the kilocalories per hour (kcal/h) unit is employed).

It will also be understood that each of the patient temperature regulation tools may be selected, deselected and/or reselected by selecting the button associated with that tool provided in frame 62 to change the prospective heat balance of the patient. For example, as shown in FIG. 8, the lower body and torso tools of the "Forced Air Warming" type have been newly selected and the standard upper body tool of the "Forced Air Warming" type has been deselected. The visual aid provided in frame 62 has been updated accordingly to show representations 83, 110, 111 of the cap, torso and lower body tools respectively together in the act of regulating the temperature of the patient. The "Passive Insulation" tab has been selected on frame 62, the "tick" icon on the cap graphic 103 providing a further indication that the cap tool remains selected. The estimated patient warming balance has also been recalculated based on the new combination of selected patient temperature regulation tools, and the indicator 94 has been updated in frame 66 accordingly to read 46 kcal/hr. The current selection of patient temperature regulation tools is thus estimated by the calculation module to provide a net heat gain to the patient.

In FIG. 9, the trauma set tool of the "Fluid Warming" type and the torso tool of the "Forced Air Warming" type have been deselected, the standard set tool of the "Fluid Warming" type has been newly selected and the standard upper body tool of the "Forced Air Warming" type has been reselected. The leggings tool of the "Passive Insulation" type has also been newly selected. As above, the visual aid provided in frame 62 has been updated accordingly, now showing representations 83, 85, 112, 113 of the cap, standard upper body tool, standard set and leggings respectively. The deselection of the trauma set and new selection of the standard set is also indicated by the selection currently displayed on frame 64 (because the "Fluid Warming" tab is currently selected). The estimated patient warming balance has also been recalculated by the calculation module 5d taking into account the new combination of selected patient temperature regulation tools, and the indication of the recalculated value has been updated in frame 66 to read −19 kcal/h (indicating a net heat loss).

FIGS. 8 and 9 also illustrate that an indication may be provided in frame 62 of whether any tools of a particular type have been selected, even when the relevant tab 86, 88, 89 relating to that type has not been selected. In the example of FIG. 8, a "tick" icon is provided in each tab 86, 88, 89 indicating that one or more tools of each of the "Forced Air Warming", "Fluid Warming" and "Passive Insulation" types have been selected.

Frame 66 also comprises additional buttons 101-106. Selecting button 101 returns the user to page 22 shown in FIG.

2, allowing a new patient's details to be entered and a new medical procedure to be selected. Selecting button 102 allows the present patient's parameters to be changed. Selecting button 104 provides more information, for example concerning the thermal properties of the tools displayed on frame 62 (or only the selected tools).

Selecting button 106 takes the user to an advanced mode, where further details concerning the patient, environmental conditions of the operating theatre and/or medical procedure can be input in order to improve the accuracy of the patient heat balance calculation. For example, environmental conditions such as ambient temperature, relative humidity, ambient pressure or velocity of down flow of air within the environment where the medical procedure will take place may be entered.

By providing both an indication of the estimated patient heat balance and a visual aid illustrating the one or more selected patient temperature regulation tools regulating the patient's temperature, it can be readily determined whether or not the selected patient temperature regulation tool is suitable for use on a particular patient and/or in a particular medical procedure. Without the visual aid, the selection of one or more patient temperature regulation tools may have thermal properties suitable for sufficiently regulating the temperature of a patient (i.e. they may yield a desired heat balance) but one or more of the selected tools may be unsuitable for use with a particular patient and/or a particular medical procedure. In the example of FIG. 6, where the Standard Upper Body tool of the "Forced Air Warming" type is selected, if the inputted medical procedure type was "Thorax Extra Large", then the selected tool would be unsuitable for use in the inputted medical procedure. Without the visual aid, this may not have been immediately apparent to the user (assuming that the warning and recommendation modules are not provided or do not disable the selection of incompatible tools).

Additionally or alternatively, a plurality of selected patient temperature regulation tools may be unsuitable for use together with each other. For example, the upper body and half upper body tools 72, 74 of the "Forced Warming" type may not be fully compatible with each other because they partially overlap. It is thus not possible to obtain the full benefit of both tools simultaneously. The visual aid provides this information (assuming that the recommendation module does not prevent the selection of this combination in the first place), which goes beyond the thermal properties of the selected patient temperature regulation tool(s), and which thus allows a more thorough (but rapid) analysis to be undertaken by a user as to whether the selected tool(s) are suitable for a particular patient and/or medical procedure and/or whether a plurality of selected patient temperature regulation tools are compatible with each other.

Even if the recommendation module prevents the selection of two incompatible tools, the visual aid provides a back-up check which is helpful to a user who may be aware of other factors not taken into account by the application 5.

The application 5 may be used by medical staff to select appropriate patient temperature regulation tools for use on a patient undergoing a medical procedure. Additionally or alternatively, the application 5 may be used as an e-learning tool. In this case, the application preferably further comprises a monitoring module which logs inputs and selections made by a user. The logged data may be used by an assessor/teacher to assess a user and/or to help the user to improve his/her performance.

The database 5a may further comprise an update module which allows a user to update the database 5a with one or more properties of one or more additional patient temperature regulation tools.

It will be understood that the application 5 need not be accessed through a browser, and that any suitable program may be used.

It will also be understood that, where one or more parameters regarding the patient and/or medical procedure are unavailable or unknown, the calculation module 5d may employ one or more standard default values to estimate the heat balance of the patient.

Although the embodiments of the invention described with reference to the drawings comprise methods performed by computer apparatus, and also computing apparatus, the invention also extends to program instructions, particularly program instructions on or in a carrier, adapted for carrying out the processes of the invention or for causing a computer to perform as the computer apparatus of the invention. Programs may be in the form of source code, object code, a code intermediate source, such as in partially compiled form, or any other form suitable for use in the implementation of the processes according to the invention. The carrier may be any entity or device capable of carrying the program instructions.

For example, the carrier may comprise a storage medium, such as a ROM, for example a CD ROM or a semiconductor ROM, or a magnetic recording medium, for example a floppy disc or hard disc. Further, the carrier may be a transmissible carrier such as an electrical or optical signal which may be conveyed via electrical or optical cable or by radio or other means. When a program is embodied in a signal which may be conveyed directly by cable, the carrier may be constituted by such cable or other device or means.

The preferred and optional features discussed above are preferred and optional features of each aspect of the invention to which they are applicable. For the avoidance of doubt, the preferred and optional features of the first and second aspects of the invention correspond to the preferred and optional features discussed in relation to the third aspect of the invention, where applicable.

Further modifications and variations may be made within the scope of the invention herein disclosed.

The invention claimed is:

1. A method of selecting one or more patient temperature regulation tools, the method comprising: providing a database storing one or more properties of each of a plurality of temperature regulation tools; selecting one or more patient temperature regulation tools from the database; calculating an estimated patient heat balance taking into account one or more of the one or more properties of the selected patient temperature regulation tool(s); providing an indication of the estimated patient heat balance; and providing a visual aid illustrating the one or more selected patient temperature regulation tools regulating the temperature of a patient, wherein the visual aid comprises a visual representation of the patient and a visual representation of the one or more selected patient temperature regulation tools in the act of regulating the patient's temperature and wherein the estimated patient heat balance is calculated at least by calculating and summing some or all of the following: the metabolic heat flow of the patient; the heat flow of uncovered body parts the heat flow of passively insulated body parts; the heat flow of actively warmed body parts; the heat flow of supplied intravenous fluids; and the heat flow of one or more surgical wounds.

2. A method of selecting one or more patient temperature regulation tools according to claim 1, wherein one or more of the one or more properties of the each of said plurality of patient temperature regulation tools are presented on a visual display prior to the step of selecting one or more patient temperature regulation tools from the database.

3. A method of selecting one or more patient temperature regulation tools according to claim 2 wherein the one or more displayed properties of the each of said plurality of patient temperature regulation tools and the visual aid are displayed on a common graphical user interface.

4. A method of selecting one or more patient temperature regulation tools according to claim 3, wherein the indication of the estimated patient heat balance is a visual indication, and wherein the visual indication of the estimated patient heat balance is displayed on the common graphical user interface simultaneously with the visual aid.

5. A method of selecting one or more patient temperature regulation tools according to claim 1, wherein the indication of the estimated patient heat balance is a visual indication.

6. A method of selecting one or more patient temperature regulation tools according to claim 1, the method further comprising selecting a plurality of patient temperature regulation tools from the database; calculating an estimated net patient heat balance taking into account one or more of the one or more properties of the plurality of selected patient temperature regulation tools; and providing a visual aid illustrating the plurality of selected patient temperature regulation tools together regulating the patient's temperature.

7. A method of selecting one or more patient temperature regulation tools according to claim 6 wherein the visual aid comprises a visual representation of the patient and a visual representation of the plurality of selected patient temperature regulation tools together in the act of regulating the patient's temperature.

8. A method of selecting one or more patient temperature regulation tools according to claim 1 further comprising: inputting one or more patient parameters; and calculating the estimated patient heat balance taking into account the inputted patient parameters.

9. A method of selecting one or more patient temperature regulation tools according to claim 8 wherein the one or more patient parameters are selected from the group of patient parameters consisting of: patient gender, patient mass, patient height and patient age.

10. A method of selecting one or more patient temperature regulation tools according to claim 1 further comprising: inputting one or more environmental conditions relating to the environment in which the medical procedure will take place; and calculating the estimated patient heat balance taking into account the inputted environmental conditions.

11. A method of selecting one or more patient temperature regulation tools according to claim 10 wherein the inputted environmental conditions are selected from a group of environmental conditions comprising: ambient temperature, relative humidity, ambient pressure or velocity of down flow of air within the environment where the medical procedure will take place.

12. A method of selecting one or more patient temperature regulation tools according to claim 1 further comprising inputting one or more variables selected from the group of variables consisting of: a type of anaesthetics; an orientation of the patient; flow rate and temperature of applied IV-fluids; and/or parameters of a surgical wound, and calculating the estimated patient heat balance taking into account one or more of said inputted variable(s).

13. A method of selecting one or more patient temperature regulation tools according to claim 1, the method further comprising inputting a type of medical procedure.

14. A method of selecting one or more patient temperature regulation tools according to claim 13 further comprising providing a warning indication if one or more of the selected one or more patient temperature regulation tools are incompatible with the inputted type of medical procedure.

15. A method of selecting one or more patient temperature regulation tools according to claim 13 further comprising: providing a recommendation of one or more patient temperature regulation tools which are compatible with said type of medical procedure; and selecting one or more recommended patient temperature regulation tools.

16. A method of selecting one or more patient temperature regulation tools according to claim 1, the method further comprising newly selecting one or more previously unselected patient temperature regulation tools and/or deselecting one or more previously selected patient temperature regulation tools in response to the indication of the estimated patient heat balance and/or visual aid; and calculating a new estimated patient heat balance taking into account the properties of the newly selected patient temperature regulation tools.

17. A method of selecting one or more patient temperature regulation tools according to claim 1 wherein the estimated heat balance is calculated by calculating the sum of a plurality of discrete heat flows.

18. A method of selecting one or more patient temperature regulation tools according to claim 17 wherein the plurality of discrete heat flows each represent one or more of the following: metabolic heat flow of a patient; heat flow of exposed body parts; heat flow of passive insulated body parts; heat flow of body parts actively warmed by one or more active patient temperature regulation tools; heat flow of supplied intravenous fluids; or heat flow of a surgical wound.

19. A method of selecting one or more patient temperature regulation tools according to claim 1, further comprising determining, prior to a particular medical procedure, whether or not the selected patient temperature regulation tool(s) are suitable for at least one of use on a particular patient and use in the particular medical procedure.

20. A method of selecting one or more patient temperature regulation tools according to claim 1, wherein the estimated patient heat balance is calculated using at least one of the following equations:

$$q_{metabolic(men)} = r.f. * \left(17.93 + 1.05 * \left(1.10 * m - \frac{128 * m^2}{(100 * l)^2}\right)\right) e^{0.0693*(T_{core} - 36.9)},$$

$$q_{metabolic(women)} = r.f. * \left(17.93 + 1.05 * \left(1.07 * m - \frac{148 * m^2}{(100 * l)^2}\right)\right) e^{0.0693*(T_{core} - 36.9)},$$

$$q_{uncovered} = A_{uncovered} * q'_{uncovered},$$

$$q_{passive\_insulate} = A_{passive\_insulated} * q'_{passive\_insulated},$$

$$q_{active\_warmed} = \left(\alpha * A_{active_{warmed}} * (T_{air} - T_{avg_{skin_{active}}}) - A_{active_{warmed}} * 2430 * 1.2706 * 10^{-6} * \left((133.32 * (1.92 * T_{avg_{skin_{active}}} - 25.3)) - 610.78 * e^{\left(\frac{T_{air}}{T_{air} + 238.3} + 17.2694\right)} * rh\right)\right),$$

-continued $$q_{IV-fluids} = q_{vol-fluid} * 10^{-6} * \frac{1}{60} * \rho_{fluid} * C_{p-fluid} * (T_{fluid} - T_{core}), \text{ and}$$

$$q_{surgical\_wound} = -A_{surgical_{wound}} *$$
$$\left(2270*1000*\frac{(25+19*v_{air})}{3600*(s.h.r-h.r)} + 3*\sqrt[4]{T_{core}-T_{amb}}*(T_{core}-T_{amb}) + \right.$$
$$\left. 5.67*10^{-8}*0.98*((T_{core}+273)^4 - (T_{amb}+273)^4)\right), \text{ wherein}$$

$A_{active\_warmed}$ is the surface area of actively warmed body parts in square meters,
$A_{passive\_insulated}$ is the surface area of passively insulated body parts,
$A_{surgical\_wound}$ is the surface area of a surgical wound in square meters,
$A_{uncovered}$ is the surface area of uncovered body parts in square meters,
$C_{p-fluid}$ is the specific heat capacity of fluid in joules per kilogram-Kelvin,
h.r is humidity ratio,
l is body length in meters,
m is body mass in kilograms,
$q'_{passive\_insulated}$ is the heat flux of passively insulated body parts,
$q'_{uncovered}$ is the heat flux of uncovered body parts in watts per square meter,
$q_{vol\_fluid}$ is volume of fluids in milliliters per minute,
r.f. is a reduction factor of metabolic heat production dependent on anaesthesia,
s.h.r is specific humidity ratio at saturation,
$T_{air}$ is the average forced air temperature that blows over the skin in degrees C.,
$T_{amb}$ is ambient temperature in degrees C.,
$T_{avg\_skin\_active}$ is the average skin temperature of the actively warmed skin in degrees C.,
$T_{core}$ core temperature of the patient,
$T_{fluid}$ is fluid temperature at the end of an IV-line connected to the patient in degrees C.,
$V_{air}$ is velocity of ambient air in meters per second, and
$\rho_{fluid}$ is density of fluid in kilograms per cubic meter.

21. A non-transitory computer readable medium storing a computer program that when executed by a computer causes the computer to execute steps for selecting one or more patient temperature regulation tools, the steps comprising: providing a database storing one or more properties of each of a plurality of temperature regulation tools; receiving a selection of one or more patient temperature regulation tools from the database; calculating an estimated patient heat balance taking into account one or more of the one or more properties of the selected patient temperature regulation tool(s); providing an indication of the estimated patient heat balance; and providing a visual aid illustrating the one or more selected patient temperature regulation tools regulating the temperature of a patient, wherein the visual aid comprises a visual representation of the patient and a visual representation of the one or more selected patient temperature regulation tools in the act of regulating the patient's temperature and wherein the estimated patient heat balance is calculated at least by calculating and summing some or all of the following: the metabolic heat flow of the patient; the heat flow of uncovered body parts; the heat flow of passively insulated body parts; the heat flow of actively warmed body parts; the heat flow of supplied intravenous fluids; and the heat flow of one or more surgical wounds.

22. A non-transitory computer readable medium according to claim 21, wherein the computer program is an e-learning application.

23. A non-transitory computer readable medium according to claim 21, further comprising determining, prior to a particular medical procedure, whether or not the selected patient temperature regulation tool(s) are suitable for at least one of use on a particular patient and use in the particular medical procedure.

24. A non-transitory computer readable medium according to claim 21, wherein the estimated patient heat balance is calculated using at least one of the following equations:

$$q_{metabolic(men)} =$$
$$r.f. * \left(17.93 + 1.05 * \left(1.10*m - \frac{128*m^2}{(100*l)^2}\right)\right) e^{0.0693*(T_{core}-36.9)},$$

$$q_{metabolic(women)} = r.f. * \left(17.93 + 1.05 * \left(1.07*m - \frac{148*m^2}{(100*l)^2}\right)\right)$$
$$e^{0.0693*(T_{core}-36.9)},$$

$$q_{uncovered} = A_{uncovered} * q'_{uncovered},$$

$$q_{passive\_insulate} = A_{passive\_insulated} * q'_{passive\_insulated},$$

$$q_{active\_warmed} =$$
$$\left(\alpha * A_{active_{warmed}} * (T_{air} - T_{avg_{skin_{active}}}) - A_{active_{warmed}} * 2430 * \right.$$
$$1.2706*10^{-6} * \left((133.32*(1.92*T_{avg_{skin_{active}}} - 25.3)) - \right.$$
$$\left.\left. 610.78 * e^{\left(\frac{T_{air}}{T_{air}+238.3}+17.2694\right)} * rh\right)\right),$$

$$q_{IV-fluids} = q_{vol-fluid} * 10^{-6} * \frac{1}{60} * \rho_{fluid} * C_{p-fluid} * (T_{fluid} - T_{core}), \text{ and}$$

$$q_{surgical\_wound} = -A_{surgical_{wound}} *$$
$$\left(2270*1000*\frac{(25+19*v_{air})}{3600*(s.h.r-h.r)} + 3*\sqrt[4]{T_{core}-T_{amb}}*(T_{core}-T_{amb}) + \right.$$
$$\left. 5.67*10^{-8}*0.98*((T_{core}+273)^4 - (T_{amb}+273)^4)\right), \text{ wherein}$$

$A_{active\_warmed}$ is the surface area of actively warmed body parts in square meters,
$A_{passive\_insulated}$ is the surface area of passively insulated body parts,
$A_{surgical\_wound}$ is the surface area of a surgical wound in square meters,
$A_{uncovered}$ is the surface area of uncovered body parts in square meters,
$C_{p-fluid}$ is the specific heat capacity of fluid in joules per kilogram-Kelvin,
h.r is humidity ratio,
l is body length in meters,
m is body mass in kilograms,
$q'_{passive\_insulated}$ is the heat flux of passively insulated body parts,
$q'_{uncovered}$ is the heat flux of uncovered body parts in watts per square meter,
$q_{vol\_fluid}$ is volume of fluids in milliliters per minute,
r.f. is a reduction factor of metabolic heat production dependent on anaesthesia,
s.h.r is specific humidity ratio at saturation,
$T_{air}$ is the average forced air temperature that blows over the skin in degrees C.,
$T_{amb}$ is ambient temperature in degrees C., $T_{avg\_skin\_active}$ is the average skin temperature of the actively warmed skin in degrees C., $T_{core}$ core temperature of the patient, $T_{fluid}$ is fluid temperature at the end of an IV-line connected to the patient in degrees C., $V_{air}$ is velocity of ambient air in meters per second, and $\rho_{fluid}$ is density of fluid in kilograms per cubic meter.

25. A computer system implementing an application for selecting one or more patient temperature regulation tools, the application comprising: a database storing one or more properties of each of a plurality of patient temperature regulation tools; an input module operable to receive a selection of one or more patient temperature regulation tools from the plurality of patient temperature regulation tools stored in the database; a calculation module operable to calculate an estimated patient heat balance taking into account one or more properties of the one or more selected patient temperature regulation tools; an indication module operable to provide an indication of the estimated patient heat balance; and a visual aid module operable to provide a visual aid illustrating the one or more selected patient temperature regulation tools regulating the temperature of a patient, wherein the visual aid comprises a visual representation of the patient and a visual representation of the one or more selected patient temperature regulation tools in the act of regulating the patient's temperature and wherein the calculation module is configured to estimate the said patient heat balance at least by calculating and summing some or all of the following: the metabolic heat flow of the patient; the heat flow of uncovered body parts; the heat flow of passively insulated body parts; the heat flow of actively warmed body parts; the heat flow of supplied intravenous fluids; and the heat flow of one or more surgical wounds.

26. A computer system implementing an application for selecting one or more patient temperature regulation tools according to claim 25 further comprising a database display module operable to provide a visual indication of each of the plurality of temperature regulation tools stored in the database.

27. A computer system implementing an application for selecting one or more patient temperature regulation tools according to claim 26 wherein the database display module and visual aid module are operable to display the visual indication and visual aid to a common graphical user interface.

28. A computer system implementing an application for selecting one or more patient temperature regulation tools according to claim 27 wherein the indication module is operable to provide a visual indication of the estimated patient heat balance and wherein the indication module is operable to display the visual indication of the estimated patient heat balance on the common graphical user interface simultaneously with the visual aid.

29. A computer system implementing an application for selecting one or more patient temperature regulation tools according to claim 25 wherein the indication module is operable to provide a visual indication of the estimated patient heat balance.

30. A computer system implementing an application for selecting one or more patient temperature regulation tools according to claim 25 wherein the input module is operable to receive an input of one or more patient parameters and wherein the calculation module is operable to calculate the estimated patient heat balance taking into account any patient parameters input to the application.

31. A computer system implementing an application for selecting one or more patient temperature regulation tools according to claim 30 wherein the one or more patient parameters comprise one or more parameters selected from the group of patient parameters consisting of: patient gender, patient mass, patient height and patient age.

32. A computer system implementing an application for selecting one or more patient temperature regulation tools according to claim 25 wherein the input module is operable to receive an input identifying one or more environmental conditions relating to an environment in which a patient will undergo a medical procedure, wherein the calculation module is operable to calculate the estimated patient heat balance taking into account one or more of said inputted environmental conditions.

33. A computer system implementing an application for selecting one or more patient temperature regulation tools according to claim 32 wherein the inputted environmental conditions comprise one or more environment conditions selected from the group of environmental conditions consisting of: temperature, relative humidity, ambient pressure or velocity of down flow of air in the environment in which the medical procedure will take place.

34. A computer system implementing an application for selecting one or more patient temperature regulation tools according to claim 25 wherein the input module is operable to receive an input identifying one or more of the following variables: a type of anaesthetics; an orientation of the patient; flow rate and temperature of applied IV-fluids; or parameters of a surgical wound, and calculating the estimated patient heat balance taking into account one or more of said inputted variable(s).

35. A computer system implementing an application for selecting one or more patient temperature regulation tools according to claim 25, wherein the input module is operable to receive an input identifying a type of medical procedure.

36. A computer system implementing an application for selecting one or more patient temperature regulation tools according to claim 35 further comprising a warning indication module operable to provide a warning indication if the selected one or more patient temperature regulation tools are incompatible with the inputted type of medical procedure.

37. A computer system implementing an application for selecting one or more patient temperature regulation tools according to claim 35 further comprising a recommendation module operable to identify recommended patient temperature regulation tools which are compatible with the inputted type of medical procedure.

38. A computer system implementing an application for selecting one or more patient temperature regulation tools according to claim 25 comprising a server computer in data communication with a client computer.

39. A computer system implementing an application for selecting one or more patient temperature regulation tools according to claim 38 wherein the server comprises: the database; the input module; the indication module; and the visual aid module.

40. A computer system implementing an application for selecting one or more patient temperature regulation tools according to claim 39 wherein the client comprises the interface module.

41. A computer system implementing an application for selecting one or more patient temperature regulation tools according to claim 38 wherein the server further comprises the calculation module.

42. A computer system implementing an application for selecting one or more patient temperature regulation tools according to claim 25 further comprising a determination module operable to determine, prior to a particular medical procedure, whether or not the selected patient temperature regulation tools are suitable for at least one of use on a particular patient and use in the particular medical procedure.

43. A computer system implementing an application for selecting one or more patient temperature regulation tools according to claim 25, wherein the calculation module is configured to estimate the patient heat balance using at least one of the following equations:

$$q_{metabolic(men)} = r.f. * \left(17.93 + 1.05 * \left(1.10 * m - \frac{128 * m^2}{(100 * l)^2}\right)\right) e^{0.0693*(T_{core}-36.9)},$$

$$q_{metabolic(women)} = r.f. * \left(17.93 + 1.05 * \left(1.07 * m - \frac{148 * m^2}{(100 * l)^2}\right)\right) e^{0.0693*(T_{core}-36.9)},$$

$$q_{uncovered} = A_{uncovered} * q'_{uncovered},$$

$$q_{passive\_insulate} = A_{passive\_insulated} * q'_{passive\_insulated},$$

$$q_{active\_warmed} = \left(\alpha * A_{active_{warmed}} * (T_{air} - T_{avg_{skin_{active}}}) - A_{active_{warmed}} * 2430 * \right.$$
$$1.2706 * 10^{-6} * \left((133.32 * (1.92 * T_{avg_{skin_{active}}} - 25.3)) - \right.$$
$$\left.\left. 610.78 * e^{\left(\frac{T_{air}}{T_{air}+238.3}+17.2694\right)} * rh\right)\right),$$

$$q_{IV-fluids} = q_{vol-fluid} * 10^{-6} * \frac{1}{60} * \rho_{fluid} * C_{p-fluid} * (T_{fluid} - T_{core}), \text{ and}$$

$$q_{surgical\_wound} = -A_{surgical_{wound}} *$$
$$\left(2270 * 1000 * \frac{(25 + 19 * v_{air})}{3600 * (s.h.r - h.r)} + 3 * \sqrt[4]{T_{core} - T_{amb}} * (T_{core} - T_{amb}) + \right.$$
$$\left. 5.67 * 10^{-8} * 0.98 * ((T_{core} + 273)^4 - (T_{amb} + 273)^4)\right), \text{ wherein}$$

$A_{active\_warmed}$ is the surface area of actively warmed body parts in square meters, $A_{passive\_insulated}$ is the surface area of passively insulated body parts, $A_{surgical\_wound}$ is the surface area of a surgical wound in square meters, $A_{uncovered}$ is the surface area of uncovered body parts in square meters, $C_{p\text{-}fluid}$ is the specific heat capacity of fluid in joules per kilogram-Kelvin, h.r is humidity ratio, l is body length in meters, m is body mass in kilograms, $q'_{passive\_insulated}$ is the heat flux of passively insulated body parts, $q'_{uncovered}$ is the heat flux of uncovered body parts in watts per square meter, $q_{vol\_fluid}$ is volume of fluids in milliliters per minute, r.f. is a reduction factor of metabolic heat production dependent on anaesthesia, s.h.r is specific humidity ratio at saturation, $T_{air}$ is the average forced air temperature that blows over the skin in degrees C., $T_{amb}$ is ambient temperature in degrees C., $T_{avg\_skin\_active}$ is the average skin temperature of the actively warmed skin in degrees C., $T_{core}$ core temperature of the patient, $T_{fluid}$ is fluid temperature at the end of an IV-line connected to the patient in degrees C., $V_{air}$ is velocity of ambient air in meters per second, and $\rho_{fluid}$ is density of fluid in kilograms per cubic meter.

\* \* \* \* \*